United States Patent
Tass et al.

(10) Patent No.: US 10,850,105 B2
(45) Date of Patent: Dec. 1, 2020

(54) DEVICE AND METHOD FOR AN EFFECTIVE INVASIVE MULTI-SEGMENT NEUROSTIMULATION

(71) Applicant: FORSCHUNGSZENTRUM JÜLICH GMBH, Jülich (DE)

(72) Inventors: Peter Alexander Tass, Tegernsee (DE); Markus Haller, Nyon (CH)

(73) Assignee: FORSCHUNGSZENTRUM JÜLICH GMBH, Jülich (DE)

(*) Notice: Subject to any disclaimer, the term of this patent is extended or adjusted under 35 U.S.C. 154(b) by 215 days.

(21) Appl. No.: 16/066,819

(22) PCT Filed: Dec. 29, 2016

(86) PCT No.: PCT/EP2016/082797
§ 371 (c)(1),
(2) Date: Jun. 28, 2018

(87) PCT Pub. No.: WO2017/114878
PCT Pub. Date: Jul. 6, 2017

(65) Prior Publication Data
US 2019/0001140 A1    Jan. 3, 2019

(30) Foreign Application Priority Data
Dec. 29, 2015   (DE) .................. 10 2015 122 888

(51) Int. Cl.
*A61N 1/36* (2006.01)
*A61N 5/06* (2006.01)
(Continued)

(52) U.S. Cl.
CPC ....... *A61N 1/36185* (2013.01); *A61N 1/0534* (2013.01); *A61N 1/0551* (2013.01);
(Continued)

(58) Field of Classification Search
CPC ............ A61N 1/36185; A61N 1/36178; A61N 1/36064; A61N 1/36082; A61N 1/0551;
(Continued)

(56) References Cited

U.S. PATENT DOCUMENTS 7,917,221 B2 *   3/2011   Tass ................. A61N 1/36135
                                                       607/45
2009/0118787 A1 *   5/2009   Moffitt ............. A61N 1/36139
                                                       607/45

FOREIGN PATENT DOCUMENTS

| DE | 102009025407 A1 | 12/2010 |
| DE | 102012002437 A1 | 8/2013 |
| EP | 1944059 A2 | 7/2008 |

OTHER PUBLICATIONS

PCT/EP2016/082797 International Search Report dated Apr. 12, 2017.

* cited by examiner

Primary Examiner — Michael W Kahelin
(74) Attorney, Agent, or Firm — Lowe Graham Jones PLLC; Bruce E. Black

(57) ABSTRACT

A device is provide for stimulating neurons. The device includes a stimulation unit that is implantable into a patient's body and that includes multiple stimulation elements for stimulating neurons in a target area of the brain and/or spinal cord of the patient with stimuli. Moreover, the device includes a control unit that actuates the stimulation unit such that multiple groups of stimulation elements generate respective stimuli. In this aspect, each group includes multiple stimulation elements of the stimulation unit with two or more of the groups generating sequences of stimuli in a repetitive manner in a respective time pattern which includes successive cycles. Furthermore, the sequences of stimuli generated by the two or more groups differ in terms of the (Continued)

number of cycles in which the sequence in which the stimulation elements generate the stimuli within one sequence is constant and/or in terms of the duration of respective cycles.

13 Claims, 9 Drawing Sheets

(51) Int. Cl.
    *A61N 1/05*     (2006.01)
    *A61N 5/067*     (2006.01)

(52) U.S. Cl.
    CPC ..... *A61N 1/36064* (2013.01); *A61N 1/36082* (2013.01); *A61N 1/36139* (2013.01); *A61N 1/36167* (2013.01); *A61N 1/36178* (2013.01); *A61N 5/0601* (2013.01); *A61N 5/0622* (2013.01); *A61N 2005/063* (2013.01); *A61N 2005/067* (2013.01); *A61N 2005/0612* (2013.01); *A61N 2005/0652* (2013.01)

(58) Field of Classification Search
    CPC ................ A61N 5/0622; A61N 1/0534; A61N 2005/0652; A61N 2005/067
    See application file for complete search history.

Fig.10
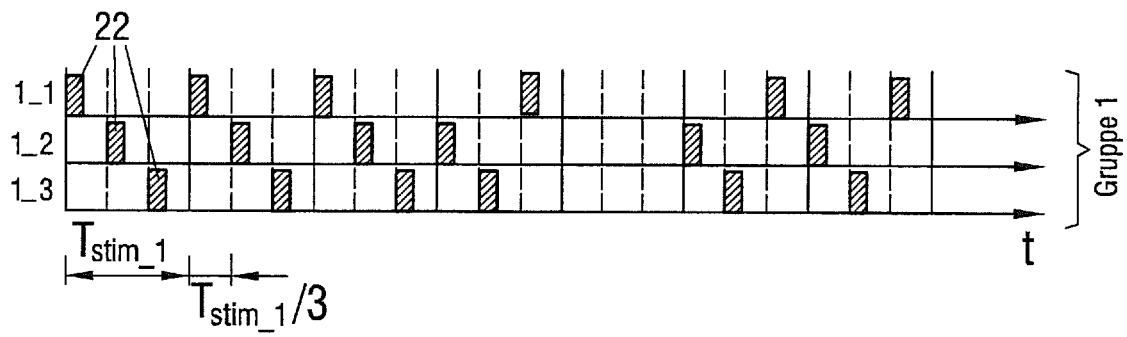
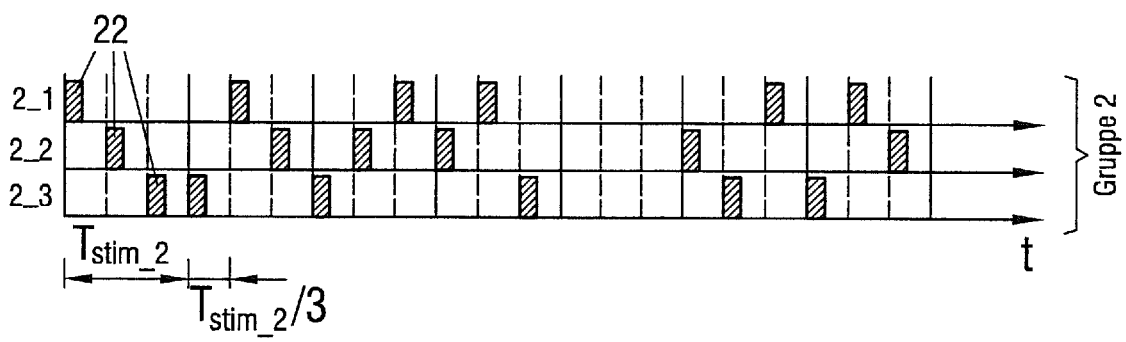
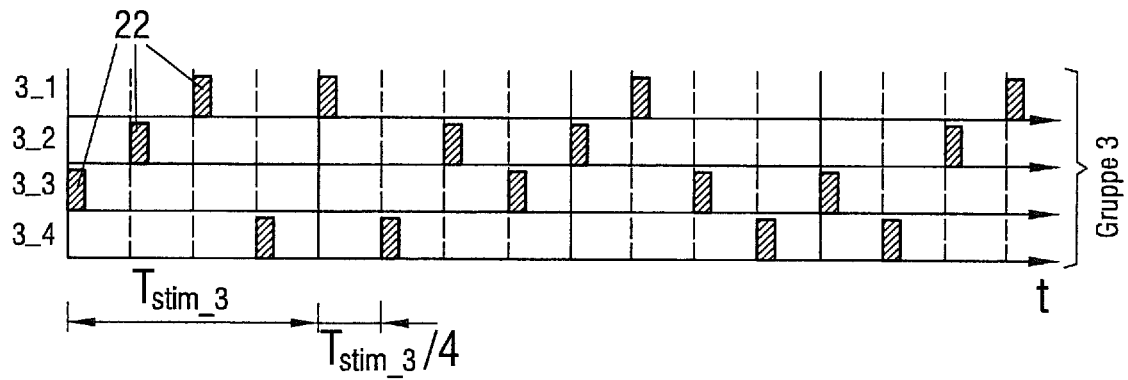

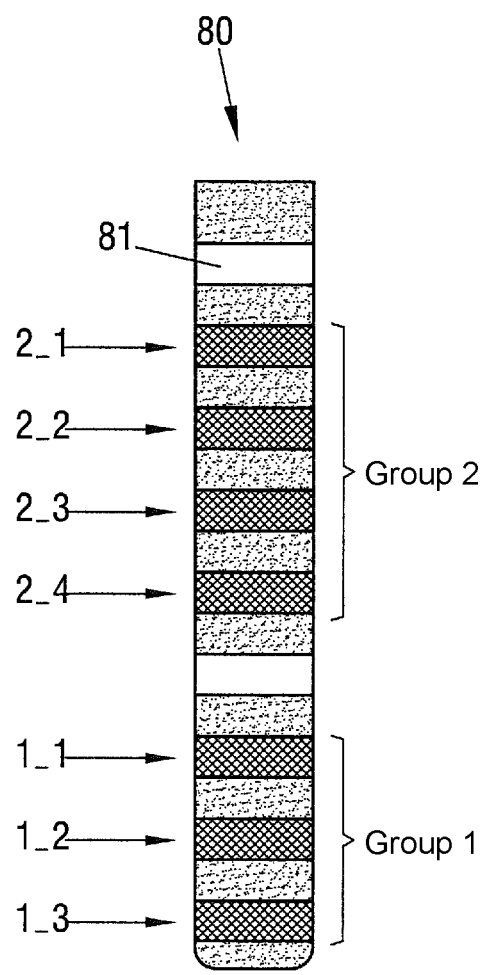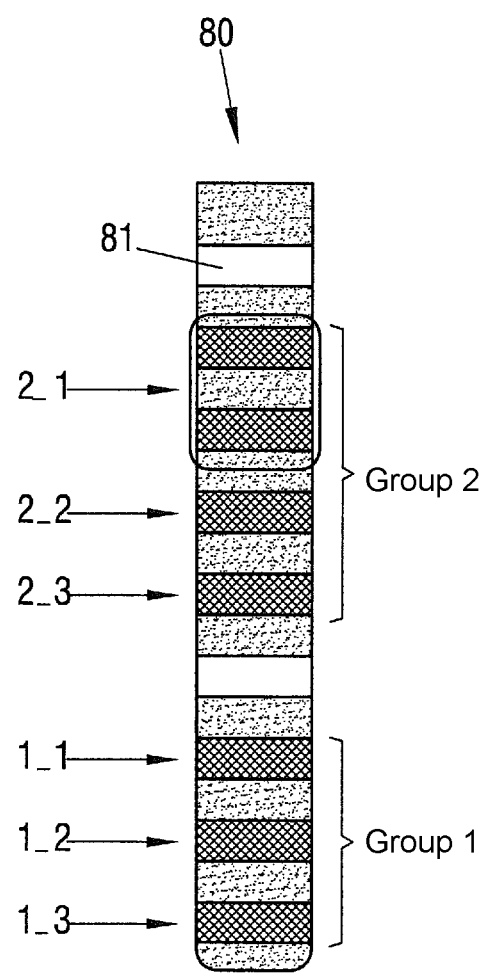

DEVICE AND METHOD FOR AN EFFECTIVE INVASIVE MULTI-SEGMENT NEUROSTIMULATION

CROSS REFERENCE TO RELATED APPLICATIONS

This application is a 35 U.S.C. § 371 National Phase of PCT Application No. PCT/EP2016/082797 filed Dec. 29, 2016, which claims benefit to DE Application No. 102015122888.2 filed Dec. 29, 2015, the disclosure of each of which is hereby incorporated by reference in their entirety.

TECHNICAL FIELD

The invention relates to a device and a method for effective, invasive, multi-segment neurostimulation.

BACKGROUND

In patients with neurological or psychiatric illnesses, e.g., Parkinson's disease, essential tremor, epilepsy, functional disorders after stroke, dystonia, or obsessive-compulsive disorders, nerve cell assemblies in circumscribed regions of the brain, e.g., of the thalamus and the basal ganglia, are pathologically, e.g., excessively synchronously, active. In this case, a large number of neurons synchronously form action potentials, i.e., the neurons involved fire excessively synchronously. In healthy persons, on the other hand, the neurons in these brain sectors fire qualitatively differently, e.g., in an uncorrelated manner.

In Parkinson's disease, the pathologically synchronous activity changes the neuronal activity in other brain sectors, e.g., in areas of the cerebral cortex such as the primary motor cortex. In this respect, the pathologically synchronous activity in the region of the thalamus and of the basal ganglia, for example, imposes its rhythm on the cerebral cortex areas such that, ultimately, the muscles controlled by these areas develop pathological activity, e.g., a rhythmic trembling (tremor).

Deep brain stimulation is used to treat Parkinson's patients who cannot be sufficiently treated by medication. In this case, deep electrodes are implanted in specific brain sectors, e.g., in the subthalamic nucleus. An electrical stimulation is carried out via the deep electrodes to relieve the symptoms. With the standard high-frequency stimulation for treating Parkinson's disease, a so-called high-frequency permanent stimulation is carried out at frequencies of more than 100 Hz. This kind of treatment has no long-lasting therapeutic effects (cf. P. Temperli, J. Ghika, J.-G. Villemure, P. Burkhard, J. Bogousslaysky, and F. Vingerhoets: How do Parkinsonian signs return after discontinuation of subthalamic DBS? Neurology 60, 78 (2003)). "Coordinated reset" stimulation (CR stimulation) manages with less stimulation, e.g., stimulation current, and can additionally have long-lasting therapeutic effects (cf. P. A. Tass, L. Qin, C. Hauptmann, S. Doveros, E. Bezard, T. Boraud, W. G. Meissner: Coordinated reset neuromodulation has sustained after-effects in Parkinsonian monkeys. Annals of Neurology 72, 816-820 (2012); I. Adamchic, C. Hauptmann, U. B. Barnikol, N. Pawelcyk, O. V. Popovych, T. Barnikol, A. Silchenko, J. Volkmann, G. Deuschl, W. Meissner, M. Maarouf, V. Sturm, H.-J. Freund, P. A. Tass: Coordinated Reset Has Lasting Aftereffects in Patients with Parkinson's Disease. Movement Disorders 29, 1679 (2014)).

With other diseases, e.g., epilepsy, that cannot be sufficiently treated with medication, different electrodes, e.g., epicortical or epidural electrodes, are also implanted in addition to deep electrodes. With further diseases, e.g., chronic pain syndromes, it is customary to stimulate the spinal cord not only by means of deep electrodes in the brain, but also by means of epidural electrodes, for example. In contrast to CR stimulation, most other types of stimulation have no long-lasting therapeutic effects.

Therapeutic effects can also be achieved by direct stimulation of the brain tissue or spinal cord by light, e.g., via implanted light guides. Different spatiotemporal stimulation patterns, such as CR stimulation, can also be used in this respect.

In order to reduce the side effects of electrical stimulation, which are, in particular, caused by anatomical inhomogeneities, multi-channel electrodes are used (cf. H. C. Martens, E. Toader, M. M. Decre, et al.: Spatial steering of deep brain stimulation volumes using a novel lead design. Clinical neurophysiology 122, 558-566 (2011); J. Buhlmann, L. Hofmann, P. A. Tass, C. Hauptmann: Modeling of a segmented electrode for desynchronising deep brain stimulation. Frontiers in Neuroengineering 4, 15 (2011)). Such multi-channel electrodes aim to limit the traditional high-frequency stimulation as much as possible to the target sector, e.g., when the deep electrodes are placed unfavourably, in order to not also stimulate neighbouring structures.

Even though deep brain stimulation by means of invasive CR stimulation makes long-lasting therapeutic effects possible, this approach has limitations. CR stimulation can cause side effects, e.g., as a result of the undesired stimulation of neighbouring structures in consequence of the spreading of stimuli, e.g., stimulation current, into regions outside the target sector or as a result of the simultaneous stimulation of structures, e.g., of fibre bundles, in the respective target sector, which is difficult to avoid for anatomical reasons (cf. C. Moreau, L. Defebvre, A. Destee, et al.: STN-DBS frequency effects on freezing of gait in advanced Parkinson disease. Neurology 71, 80-84 (2008); M. Jahanshahi, I. Obeso, C. Baunez, et al.: Parkinson's disease, the subthalamic nucleus, inhibition, and impulsivity. Movement Disorders 30, 128-140 (2015)). Such situations arise, for example, as a result of the characteristic close anatomical proximity of the target point aimed for during electrode implantation and other anatomical structures, the stimulation of which results in side effects, as a result of specific, individual, anatomical boundary conditions (e.g., in the sense of the location of blood vessels, which must be treated with care during the implantation of the electrodes), or as a result of sub-optimal or even incorrect electrode implantation.

Furthermore, the therapeutic effect in some patients occurs with a delay and/or does not develop fully. Spatially extended synchronisation processes can react differently to the same stimuli at different locations, e.g., as a result of different dynamic characteristics—in particular, different dominant frequencies of the oscillatory activity. The effectiveness of the CR stimulation is reduced, in particular, if synchronisation processes that are spatially inhomogeneous with respect to their dominant frequency are stimulated with stimuli of the same rhythmicity, i.e., stimulation period. A spatially inhomogeneous distribution of the dominant frequencies of neuronal synchronisation processes can, for example, result from the somatotopic arrangement of neurons: the neurons of different spatial subregions are responsible for different body and limb parts. Different segments of limbs, e.g., hand vs. upper arm, have different mechanical natural frequencies, which promotes the occurrence of different dominant frequencies in case of illness.

The two limitations described above are based upon the fact that an optimal stimulation is made difficult by anatomical and functional inhomogeneities. The term, "anatomical inhomogeneities", in this case means that the proportion of neurons of a certain type and, in particular, the proportion of fibres that run through the target sector are typically spatially inhomogeneous. Functional inhomogeneities are due to the fact that the characteristic dynamic parameters in different regions can sometimes vary strongly in spatially extended neuronal synchronisation processes. For example, the dominant frequencies, e.g., in the sense of a spectral analysis, can be distributed spatially inhomogeneously and, moreover, vary strongly over time.

SUMMARY OF THE INVENTION

The invention is based upon the aim of specifying a device and a method for the stimulation of neurons, with which device and method the stimulation can be significantly better adapted to the local anatomical and functional circumstances than in the prior art. Side effects are to be significantly reduced and the therapeutic effect is to be significantly improved thereby.

The aim underlying the invention is achieved by the features of the independent claims. Advantageous developments and embodiments of the invention are specified in the dependent claims.

BRIEF DESCRIPTION OF THE DRAWINGS

The invention is explained in more detail below by way of example with reference to the drawings. Shown are:

FIG. 10 illustrates a schematic illustration of a multi-segment CR stimulation;

FIGS. 16 & 17 illustrates schematic illustrations of a multi-channel electrodes with groups and subgroups of contacts.

DETAILED DESCRIPTION

Figure 1:
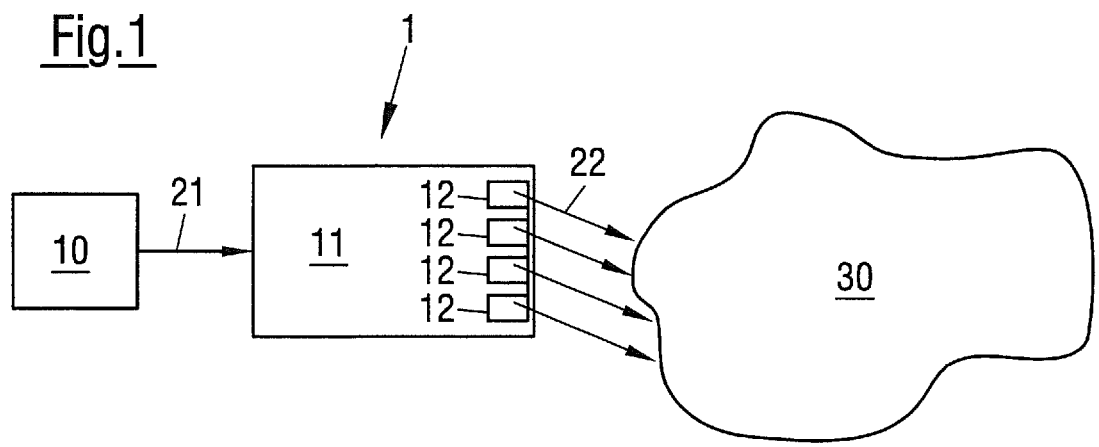
FIG. 1 illustrates a schematic illustration of a device for suppressing a pathologically synchronous and oscillatory neuronal activity and, in particular, for desynchronising neurons having a pathologically synchronous and oscillatory activity in accordance with a first embodiment.

FIG. 1 schematically shows a device 1 for stimulating neurons having a pathologically synchronous and oscillatory neuronal activity. The device 1 consists of a control unit 10 and a stimulation unit 11 which has a plurality of stimulation elements 12. FIG. 1 shows four stimulation elements 12 by way of example. The stimulation unit 11 can naturally, however, also have a different number of stimulation elements 12. In the case of electrical stimulation, the stimulation elements 12 can, for example, be stimulation contact surfaces of one or more electrodes for applying electrical stimuli. If stimulation takes place optically, light guides can, for example, be used as stimulation elements 12, in order to stimulate the neuronal tissue with light stimuli at the desired points.

During operation of the device 1, the control unit 10 controls the stimulation unit 11. To this end, the control unit 10 generates control signals 21, which are received by the stimulation unit 11.

The stimulation unit 11 is surgically implanted into the body of the patient and generates, on the basis of the control signals 21, stimuli 22—in particular, electrical and/or optical stimuli 22—which are administered to a target area 30 in the brain and/or spinal cord of the patient. The stimuli 22 are designed to suppress the pathologically synchronous and oscillatory neuronal activity upon administration to the patient and, in particular, to desynchronise the neurons having the pathologically synchronous and oscillatory activity.

The control unit 10 can be a non-invasive unit, i.e., it is outside the body of the patient during operation of the device 1 and is not surgically implanted into the body of the patient.

The device 1 and the device 2 described further below in connection with FIG. 7 can, in particular, be used to treat neurological or psychiatric diseases, e.g., Parkinson's disease, essential tremor, tremor resulting from multiple sclerosis as well as other pathological tremors, dystonia, epilepsy, depression, locomotor disorders, cerebellar diseases, obsessive-compulsive disorders, dementia, Alzheimer's, Tourette's syndrome, autism, functional disorders after stroke, spasticity, tinnitus, sleep disorders, schizophrenia, irritable bowel syndrome, addiction diseases, borderline personality disorder, attention deficit syndrome, attention deficit hyperactivity syndrome, pathological gambling, neuroses, bulimia, anorexia, eating disorders, burnout syndrome, fibromyalgia, migraine, cluster headache, general headache, neuralgia, ataxia, tic disorder or hypertension, as well as other diseases that are characterised by pathologically increased neuronal synchronisation.

The aforementioned diseases can be caused by a disorder of the bioelectrical communication of neuronal assemblies that are connected in specific circuits. In this respect, a neuronal population continuously generates pathological neuronal activity and possibly a pathological connectivity (network structure) associated therewith. In this respect, a large number of neurons synchronously form action potentials, i.e., the neurons involved fire excessively synchronously. In addition, the pathological neuronal population has an oscillatory neuronal activity, i.e., the neurons fire rhythmically. In the case of neurological or psychiatric diseases, the mean frequency of the pathological rhythmic activity of the affected neuronal assemblies lies approximately in the range of 1 to 30 Hz, but can also be outside this range. In healthy people, on the other hand, the neurons fire qualitatively differently, e.g., in an uncorrelated manner.

Figure 2:
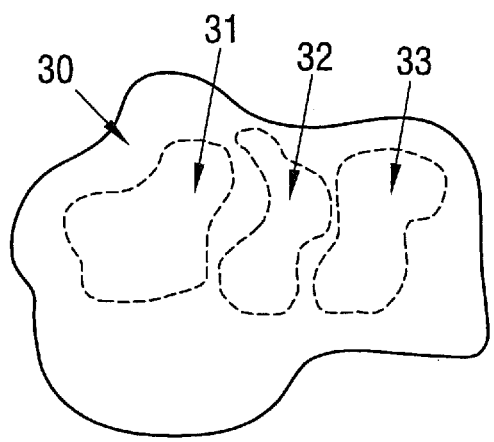
FIG. 2 illustrates a schematic illustration of a target area with spatially separate neuronal synchronisation processes.

Spatially extended pathological neuronal synchronisation processes can be spatially inhomogeneous and, in particular, need not be spatially coherent. They can consist of spatially separate, but synaptically connected subregions. This is shown by way of example in FIG. 2. Shown schematically there is the target area 30, in which spatially separate neuronal synchronisation processes are situated in different subregions 31, 32, and 33.

Figure 3:
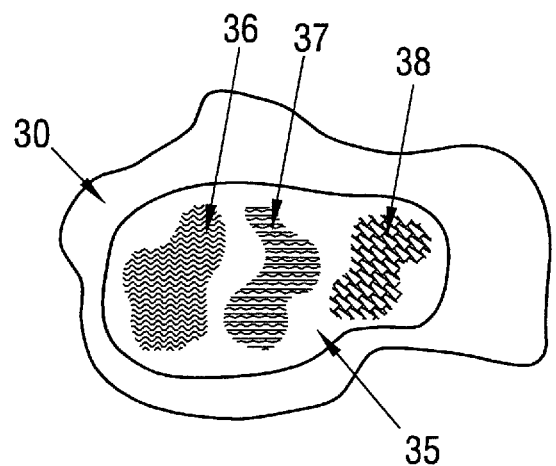
FIG. 3 illustrates a schematic illustration of a target area with a spatially circumscribed region in which different subregions of neuronal synchronisation processes are located.

Pathological neuronal synchronisation processes can also be circumscribed spatially, but nonetheless be spatially inhomogeneous as a result of functional characteristics. One example of such synchronisation processes is shown in FIG. 3. In this case, different subregions 36, 37, and 38 of the neuronal synchronisation process are situated in a spatially circumscribed region 35.

Different dominant frequencies of the pathological oscillation of the neurons can prevail in the subregions 31 to 33 or 36 to 38. The respective dominant frequencies or other characteristic functional features can be determined by means of multi-channel derivatives. In doing so, local field potentials (LFP) are, for example, derived via the respective contact points. Single-cell derivations may also be carried out. The person skilled in the art knows how the underlying oscillatory neuronal activities are estimated using standard data analysis methods.

Figure 4:
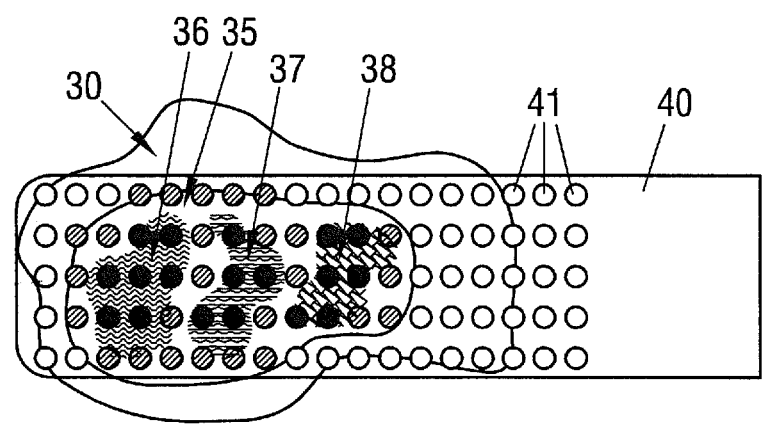
FIG. 4 illustrates a schematic illustration of a multi-channel electrode for deriving measurement signals and/or directly stimulating the target area.

FIG. 4 schematically shows a multi-channel electrode 40, which serves as stimulation unit 11 and has a plurality of electrically conductive contacts or stimulation contact surfaces 41, which are arranged in an array and constitute the stimulation elements 12. In the present embodiment, the contacts 41 can be controlled individually so that a desired electrical stimulus 22 can be applied via each contact 41. The contacts 41 can, moreover, also be used to measure neuronal activity, as described further below in even more detail.

By way of example, FIG. 4 shows an electrical stimulation of the subregions 36 to 38 of the target area 30, in which different dominant frequencies of the pathological neuronal oscillation prevail. The spatial profile of the amplitude of the signals or spectral power measured via the respective contacts 41 is shown schematically by a different fill of the contacts 41. The darker the fill of a contact 41 is, the higher is the dominant frequency of the pathologically synchronous oscillation measured in the neuronal tissue at the affected location.

In case of direct stimulation, the contacts 41 are placed directly on the region 35 to be stimulated. In doing so, the somata, axones, and dendrites of the respective neuron populations can be stimulated directly. In the present example, the subregions 36 to 38 are stimulated via the darkly-filled contacts 41 assigned to the respective subregions 36 to 38. A group of contacts 41 is in this case assigned to each of the subregions 36 to 38.

Figure 5:
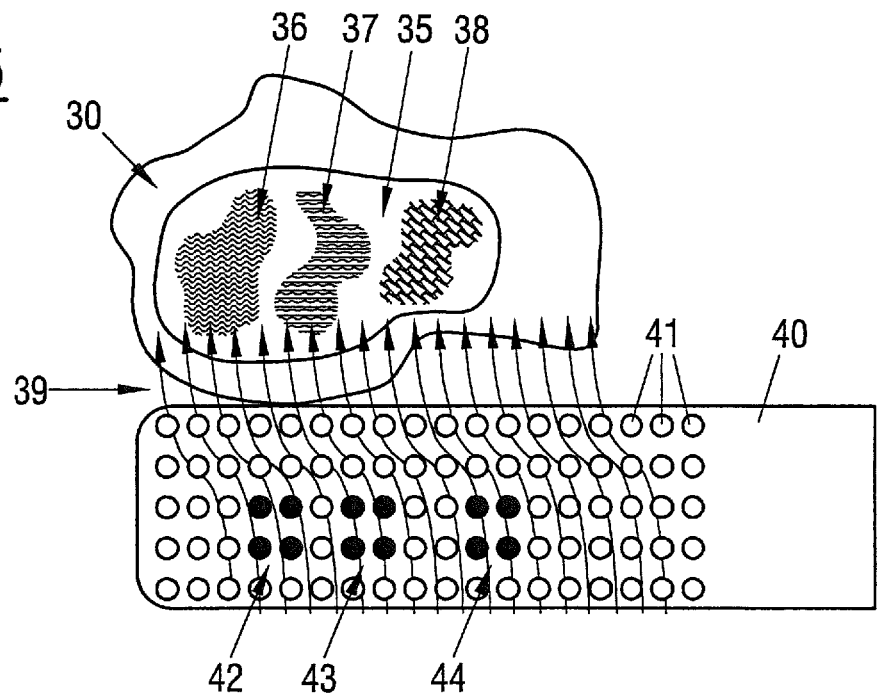
FIG. 5 illustrates a schematic illustration of a multi-channel electrode for indirectly stimulating the target area.

Spatially separate subregions or subregions separated by functional characteristics can also be stimulated indirectly via different contact groups, as shown by way of example in FIG. 5. The multi-channel electrode 40 is in this case not placed directly on the subregions 36 to 38; rather, fibres 39 that lead to the respective subregions 36 to 38 and/or originate therefrom are stimulated. In the exemplary embodiment shown in FIG. 5, groups 42, 43, and 44 are respectively formed from several contacts 41, and the afferent fibres 39 leading to the subregions 36, 37, or 38 are stimulated with the groups 42, 43, and 44 respectively. The contacts 41 of groups 42 to 44 are shown with a dark fill in FIG. 5.

Figure 6:
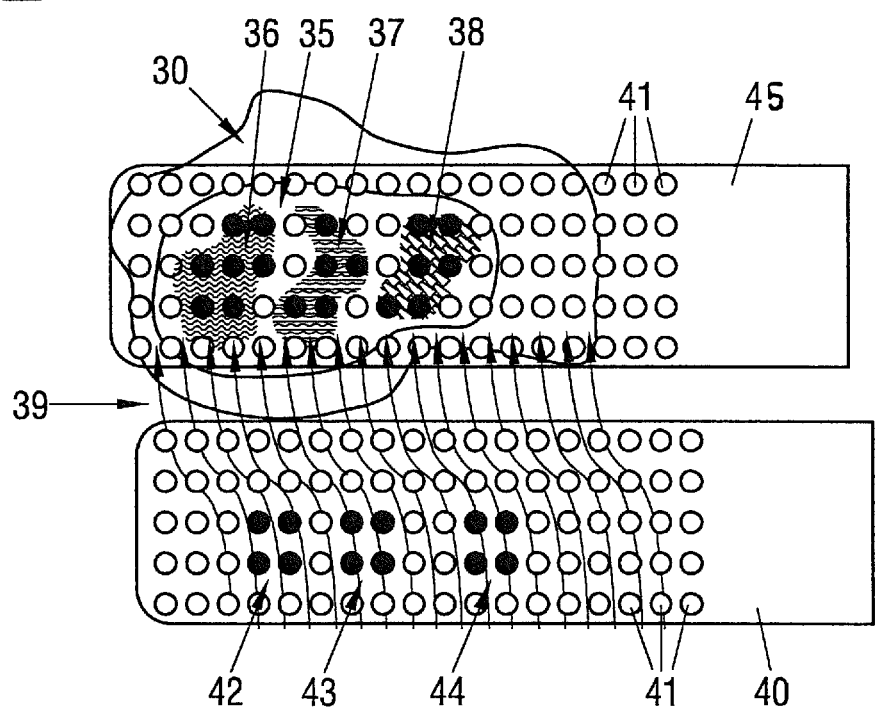
FIG. 6 illustrates a schematic illustration of two multi-channel electrodes for deriving measurement signals and/or directly or indirectly stimulating the target area.

Combinations of direct and indirect stimulation can also be carried out. Such a combination is shown by way of example in FIG. 6. In this case, another multi-channel electrode 45 is directly placed over the region 35, in addition to the indirectly stimulating multi-channel electrode 40 of FIG. 5. In case of a combined direct and indirect stimulation, some of the subregions 36 to 38 can be stimulated exclusively directly; the others can be stimulated exclusively indirectly. The subregions 36 and 38 can, for example, be stimulated via the contacts 41 of the multi-channel electrode 45; the subregion 37, on the other hand, can be stimulated via the contacts 41 of group 43 of the multi-channel electrode 40. In principle, a simultaneous and/or alternating combined direct and indirect stimulation of the same subregion can also take place.

In the case of the direct and/or indirect electrical stimulation, the types known to the person skilled in the art of bipolar stimulation between pairs of contacts 41, as well as of unipolar stimulation between contacts 41 and a common ground, can be used.

The device 1 shown in FIG. 1 for stimulating neurons having a pathologically synchronous and oscillatory neuronal activity carries out a so-called "open loop" stimulation, i.e., a stimulation without sensors, which are used for feedback and/or control of the stimulation.

Figure 7:
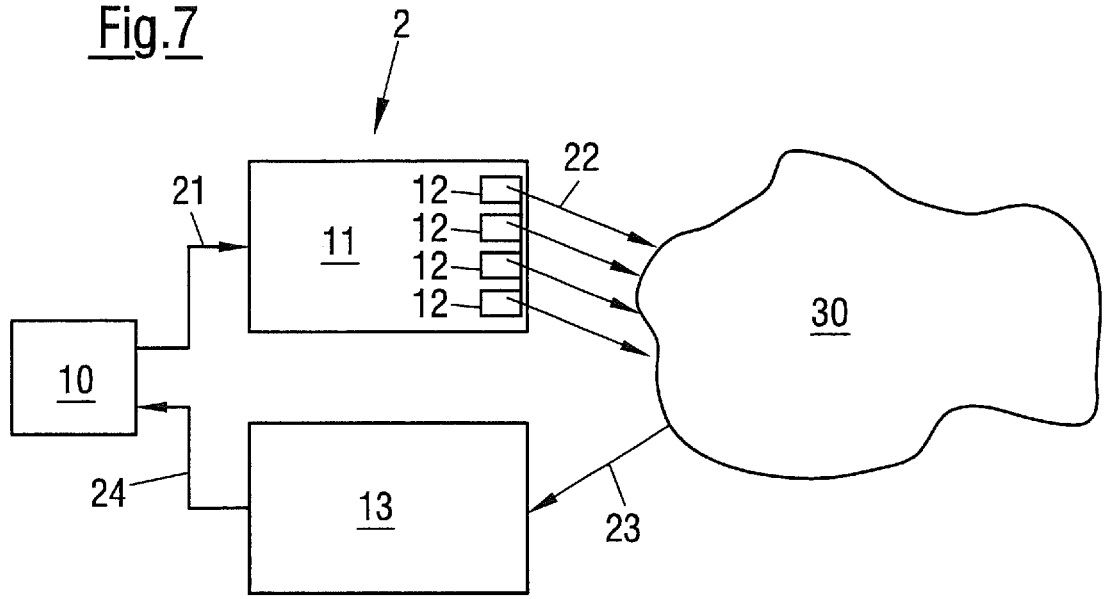
FIG. 7 illustrates a schematic illustration of a device for suppressing a pathologically synchronous and oscillatory neuronal activity and, in particular, for desynchronising neurons having a pathologically synchronous and oscillatory activity in accordance with a second embodiment.

FIG. 7 schematically shows a device 2 for stimulating neurons having a pathologically synchronous and oscillatory neuronal activity, with which device a "closed loop" stimulation can be carried out. The device 2 is a development of device 1 shown in FIG. 1 and, like device 1, contains a control unit 10 and an implantable stimulation unit 11, which have the same functions and properties as the control and stimulation units 10, 11 of device 1 described above.

Device 2 additionally comprises a measuring unit 13. The measuring unit 13 receives one or more measurement signals 23 measured on the patient, converts them into electrical signals 24 where applicable, and transmits them to the control unit 10. The neuronal activity in the stimulated target area 30 or in a sector connected to the target area 30 can, in particular, be measured by means of the measuring unit 13, wherein the neuronal activity of this sector sufficiently closely correlates with the neuronal activity of the target sector 30. In the case of spatially extended synchronisation processes, the dominant frequency of the oscillatory activity, in particular, can be measured by means of the measuring unit 13 at different points of the target area 30. A non-neuronal, e.g., muscular, activity or the activation of the autonomous nervous system can also be measured by means of the measuring unit 13 if this activity or activation is sufficiently closely correlated with the neuronal activity of the target sector. The stimulation effect achieved by the stimuli 22 can furthermore be monitored by means of the measuring unit 13.

The measuring unit 13 contains one or more sensors that, in particular, allow for the amplitude of the pathologically oscillatory activity to be recorded.

The sensors can be implanted into the body of the patient. For example, epicortical electrodes, deep brain electrodes for measuring, for example, local field potentials, subdural or epidural brain electrodes, subcutaneous EEG electrodes, and subdural or epidural spinal cord electrodes can serve as invasive sensors. The deep electrodes for measuring the local field potentials can also be combined structurally with or even be identical to the multi-channel electrodes used for stimulation. The contacts of the multi-channel electrodes can be placed such that they can derive relevant neuronal feedback signals. In the embodiment shown in FIG. 6, the neuronal activity can, for example, be derived via the multi-channel electrode 45, while stimulation takes place via the same multi-channel electrode 45 directly and/or via the multi-channel electrode 40 indirectly.

Alternatively, non-invasive sensors can be used, e.g., chronically or intermittently used electroencephalography (EEG) or electromyography (EMG) electrodes, or magnetoencephalography (MEG) sensors. The neuronal activity can also be determined by detecting characteristic movement patterns, such as tremor, akinesia, or epileptic seizures, with the aid of an accelerometer or gyroscope, or, indirectly, by measuring the activation of the autonomous nervous system by means of a measurement of the skin resistance. Mental state values that are input into portable devices, e.g., smartphones, by the patient can also be used to monitor the stimulation success. Such mental state values can also be determined via short questionnaires.

The control unit 10 processes the signals 24, e.g., the signals 24 can be amplified and/or filtered, and analyses the processed signals 24. The control unit 10 determines, in particular, the dominant frequency of the oscillatory activity for the different subregions of the target area 30 and checks the stimulation success using the measurement signals 23 recorded in response to the application of the stimuli 22.

The stimulation of the target area 30 takes place, in particular, by means of a CR stimulation. In the brain and/or spinal cord of the patient, at least one neuronal population has a pathologically synchronous and oscillatory neuronal activity as described above. The stimulation unit 11, or the multi-channel electrodes 40, 45, stimulate(s) the pathologically active neuronal population in the brain and/or spinal cord with the electrical and/or optical stimuli 22, either directly or indirectly. In the CR stimulation, the stimuli 22 are designed such that the time-offset (or phase-shifted) stimulation with at least two stimulation elements 12 or contacts 41 brings about a desynchronisation of the pathologically synchronous activity of the neuronal population. A lowering of the coincidence rate of the neurons brought about by the stimulation can result in a lowering of the synaptic weights and thus in an unlearning of the tendency to produce pathologically synchronous activity.

The stimuli 22 administered in the CR stimulation bring about a reset of the phase of neuronal activity of the stimulated neurons in the neuronal population. By the reset, the phase of the stimulated neurons is set to or close to a specific phase value, e.g., 0°, independently of the current phase value (it is not possible in practice to set a specific phase value exactly; however, this is also not required for a successful CR stimulation). The phase of the neuronal activity of the pathological neuronal population is thus controlled by means of a targeted stimulation. Since the pathological neuronal population is stimulated at different points via the stimulation elements 12 or contacts 41, the respective phases of the neuronal activity of several subpopulations of the pathological neuronal population can be reset at different points in time by applying the stimuli 22 in a time-offset (or phase-shifted) manner by the stimulation elements 12 or contacts 41. As a result, the pathological neuronal population whose neurons were previously active synchronously and at the same frequency and phase are split into several subpopulations having different phases. After resetting the phase, the neurons in each of the subpopulations are still synchronous and also still fire with the same pathological frequency, but each of the subpopulations has that phase with respect to its neuronal activity that was imposed on it by the stimulus 22 generated by the respective stimulation element 12 or contact 41. This means that, after resetting their phases, the neuronal activities of the individual subpopulations still have an approximately sinusoidal curve at the same pathological frequency, but different phases.

As described above, the stimulation elements 12 or the contacts 41 stimulate different subpopulations with the stimuli 22. In this respect, however, it does not necessarily have to be a case of disjunctive subpopulations, i.e., subpopulations completely separate from one another. The subpopulations stimulated by the stimulation elements 12 or contacts 41 can also overlap one another.

Due to the pathological interaction between the neurons, the state with at least two subpopulations generated by the stimulation is unstable, and the total neuronal population fast approaches a state of complete desynchronisation in which the neurons fire without correlation. The desired state, i.e., the complete desynchronisation, is thus not immediately present after the time-offset (or phase-shifted) application of the phase-resetting stimuli 22, but is usually adopted within a few periods or even in less than one period of the pathological frequency.

One theory for explaining the stimulation success is based upon the fact that the ultimately desired desynchronisation is only made possible by the pathologically increased interaction between the neurons. In this respect, a self-organisation process is made use of, which is responsible for the pathological synchronisation. The same process has the effect that a division of an overall population into subpopulations with different phases is followed by a desynchronisation. In contrast thereto, no desynchronisation would take place without a pathologically increased interaction of the neurons.

Furthermore, a reorganisation of the connectivity of the disturbed neuronal networks can be achieved by the CR stimulation, so that long-lasting therapeutic effects can be brought about. The obtained synaptic conversion is of great importance for the effective treatment of neurological or psychiatric diseases.

Figure 8:
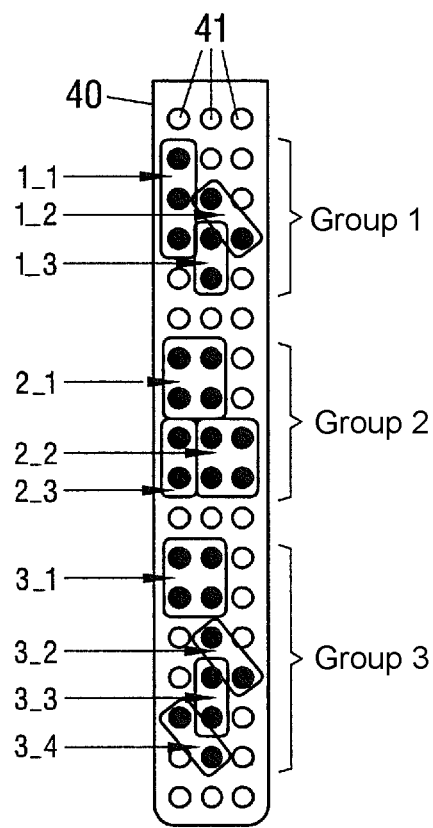
FIG. 8 illustrates a schematic illustration of a multi-channel electrode with groups and subgroups of contacts.

The stimulation patterns administered in multi-segment neurostimulation shall be described in more detail below. In analogy to FIG. 4, FIG. 8 shows by way of example a multi-channel electrode 40 having a plurality of electrically conductive contacts 41 that are arranged in an array and constitute the stimulation elements 12. In the present embodiment, the contacts 41 can be controlled individually, so that a desired electrical stimulus 22 can be applied via each contact 41. The contacts 41 can, furthermore, also be used to derive neuronal activity.

By way of example, FIG. 8 shows three groups or segments of contacts 41, which are called group 1, group 2, and group 3 and respectively comprise several contacts 41. The contacts 41 belonging to a respective group are marked by a dark fill. Groups 1 to 3 serve to directly and/or indirectly stimulate different subregions of a target area, e.g., the subregions 31 to 33 of FIG. 2 or the subregions 36 to 38 of FIG. 3, with excessively synchronous neuronal activity in the brain and/or spinal cord of a patient.

For the application of a CR stimulation, each of the groups 1 to 3 consists of several subgroups, wherein each respective subgroup can comprise one or more contacts 41. The contacts 41 belonging to a respective subgroup are marked in FIG. 8 by a border. By way of example, group 1 in FIG. 8 consists of the subgroups 1_1, 1_2, and 1_3, group 2 consists of the subgroups 2_1, 2_2, and 2_3, and group 3 consists of the subgroups 3_1, 3_2, 3_3, and 3_4. The individual stimuli 22 applied in the course of a CR sequence are administered via the subgroups. The contacts 41 or, in general, the stimulation elements 12 of each subgroup always simultaneously generate the same stimulus 22.

The stimulation via the different subgroups can take place via respectively independent power sources. For example, device 1 can have a number of power sources that is at least as large as the number of subgroups via which the stimulation takes place.

The groups can be identified by measurements and/or test stimulations. The selection of the subgroups within the respective groups can take place based upon the following criteria: (i) maximising the mutual distances between the respective or neighbouring subgroups, (ii) minimising the mutual contact zones between the respective or neighbouring subgroups, (iii) previously-known anatomical and/or physiological boundary conditions, (iv) characteristics of stimulus responses when stimulated via different subgroups, (v) optimal coverage of regions with very pronounced synchronisation, i.e., for example, large LFP amplitude according to the measurement (as illustrated in FIG. 4), and (vi) minimal spatial overlap of the tissue respectively stimulated by the different subgroups.

Figure 9:
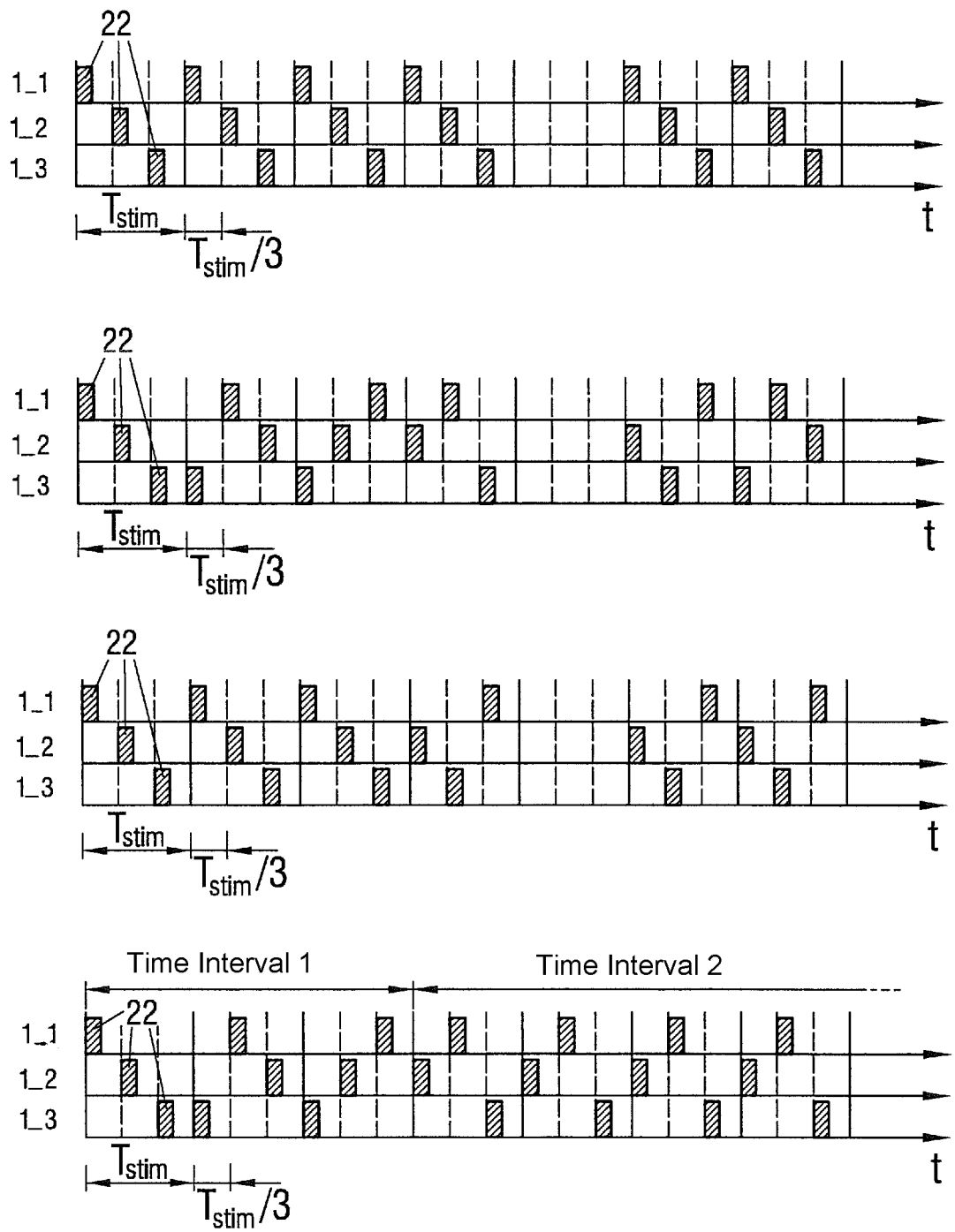
FIG. 9 illustrates schematic illustrations of different CR stimulus sequences for stimulating neurons.

A respective subregion of the target area is stimulated via each of the groups 1 to 3. On the basis of group 1 and its subgroups 1_1, 1_2, and 1_3, FIG. 9 shows by way of example four different CR stimulus sequences with which a subregion of the target area can be stimulated.

In each of the four partial figures of FIG. 9, the stimuli 22 generated by the contacts 41 of subgroups 1_1, 1_2, and 1_3 are plotted, one below the other, against the time t. The stimuli 22 are generated in a predefined time pattern that consists of consecutive cycles. In FIG. 9, the individual cycles are delineated from one another by solid vertical lines. Each cycle has the length $T_{stim}$. In each cycle in which a stimulation takes place, the subgroups 1_1, 1_2, and 1_3 together generate exactly one sequence of stimuli 22, and each of the subgroups 1_1, 1_2, and 1_3 generates exactly one stimulus 22 per sequence, i.e., each sequence in the present example comprises a progression of three, time-offset stimuli 22 that are, in particular, generated by respectively different subgroups 1_1, 1_2, and 1_3, wherein the time offset can, in particular, relate to the starting times of the stimuli 22. In the process, each contact 41 of a respective subgroup 1_1, 1_2, and 1_3 generates the same stimulus 22.

Each group i can basically contain any number $L_i$ of subgroups ($L_i \geq 2$), but all $L_i$ subgroups do not necessarily have to be used in a stimulation; for example, only a selection of $P_i$ of the $L_i$ subgroups can also generate the stimuli 22 ($2 \leq P_i \leq L_i$), wherein all $P_i$ selected subgroups then respectively generate exactly one stimulus 22 within a given sequence. For example, the $P_i$ subgroups used for stimulation can vary from cycle to cycle (or at other intervals), e.g., three different subgroups each can be selected per cycle. The number $P_i$ of the subgroups can furthermore also vary from cycle to cycle (or at other intervals), e.g., stimulation can take place in a respective cycle by means of three, four, or five different subgroups.

In the case of $P_i$ subgroups of the group i, $P_i!$ possible different sequences result, wherein each of the $P_i$ subgroups generates exactly one stimulus 22 in each of these sequences. It is conceivable to use all $P_i!$ possible sequences for the stimulation, or to select a subset of the set of $P_i!$ possible sequences for the stimulation. This subset can also vary over time according to stochastic or deterministic or mixed stochastic-deterministic rules. The progression of the sequences can be random or can be fixed before or during the stimulation.

In the first, i.e., upper, partial figure of FIG. 9, the order in which the subgroups 1_1, 1_2, and 1_3 generate the stimuli 22 within a cycle is constant. Furthermore, after a certain number of cycles, a break can be observed in which no stimuli 22 are applied. The duration of the break can, in particular, be $T_{stim}$ or a whole-number multiple of $T_{stim}$. Afterwards, the stimulation can continue in the same way as before the break.

Group 1 stimulates a certain subregion of the target area, and each of the three subgroups 1_1, 1_2, and 1_3 of group 1 stimulate a respective subpopulation of this subregion. During the cycles in which the stimuli 22 are applied, the stimulus 22 of each of the subgroups 1_1, 1_2, and 1_3 is periodically applied with period $T_{stim}$. The stimuli 22 bring about a phase reset of the neuronal activity of the respectively stimulated subpopulation. Furthermore, the time delay between stimuli 22 generated within a sequence directly after one another in time by different subgroups is $T_{stim}/3$, since three subgroups 1_1, 1_2, and 1_3 are used for the CR stimulation in the present exemplary embodiment. For the general case of N subgroups used for the stimulation, the time delay between stimuli 22 generated within a sequence directly after one another in time by different subgroups would be $T_{stim}/N$ (a deviation from this value by, for example, up to ±5% or ±10% or by an even higher percentage is also possible). The time delay $T_{stim}/N$ can relate to the starting times of the stimuli 22. The stimuli 22 generated by different subgroups can be identical except for the different starting times.

The period $T_{stim}$ that indicates the duration of a cycle, on the one hand, and the period with which unchanging sequences and the stimuli 22 generated by a respective subgroup are repeated, on the other hand, can be close to the mean period of the dominant pathological oscillation (i.e., the inverse of the dominant frequency) of the neurons in the subregion of the target area stimulated by group 1 and having the pathologically synchronous and oscillatory neuronal activity, or can differ from the mean period by up to ±5% or ±10%. The frequency $f_{stim}=1/T_{stim}$ is typically in the range of 1 to 30 Hz. The dominant frequency of the pathological oscillation of the neurons to be stimulated can be measured by means of the measuring unit 13. It is, however, also possible to use textbook values or empirical values that relate to the respective disease to be treated for the period of the pathological oscillation. An exact estimation of the optimal frequency $f_{stim}=1/T_{stim}$ can be carried out by an analysis in a sliding time window using the data analysis method known to the person skilled in the art. For example, the absolute maximum of the spectral power density in a (medically justified) predefined frequency interval can be determined in a sliding time window. Instead of the band pass filtering, other data preprocessing steps can also be used, e.g., wavelet analysis or empirical mode decomposition (EMD). Especially with temporarily noisy signals and/or noisy signals due to the suboptimal location of the sensors, an autocorrelation function can also be calculated.

In all four partial figures of FIG. 9, the phase-resetting stimuli 22 can, for example, be individual stimuli or assembled stimuli. Each stimulus 22 can, for example, consist of a pulse train of 2 to 100—in particular, 2 to 10—individual pulses. Within a pulse train, the individual pulses are repeated without interruption at a so-called intra-burst frequency in the range of 50 to 500 Hz—in particular, in the range of 100 to 200 Hz. The intra-burst frequency within a pulse train can be fixed. The pulses of a pulse train can, furthermore, be identical.

While the sequences in the first partial figure of FIG. 9 are constant, the second partial figure of FIG. 9 shows an embodiment that constitutes a development of the CR stimulation shown in the first partial figure and in which, at the beginning of each cycle, the order in which the subgroups 1_1, 1_2, and 1_3 generate the phase-resetting stimuli 22 is varied—in particular, is varied randomly. For example, the subgroups 1_1, 1_2, and 1_3 in the first cycle shown in the second partial figure of FIG. 9 generate the stimuli 22 in the order 1_1-1_2-1_3. In the second cycle, the order is 1_3-1_1-1_2 and, in the third cycle, the order is 1_3-1_2-1_1.

The third partial figure of FIG. 9 shows a development of the CR stimulation shown in the second partial figure. The essential difference for the stimulation according to the second partial figure consists in the sequences being varied only very slowly in the CR stimulation shown in the third partial figure. It is, in particular, provided that the order in which the subgroups 1_1, 1_2, and 1_3 generate the phase-resetting stimuli 22 within a sequence be kept constant for at least 20 consecutively generated sequences and only be varied thereafter. A CR stimulation with such slowly varying sequences is significantly superior to the CR stimulation shown in the second partial figure of FIG. 9, since its desired, i.e., therapeutic, stimulation effect (i) is more strongly pronounced, (ii) is significantly less varied from stimulation epoch to stimulation epoch, and (iii) is significantly more robust with respect to the fluctuations of the stimulus intensity, to the fluctuations of characteristic parameters of the body or nervous system, and, in particular, to variations of the initial values.

It can be provided, as described above, that the sequences remain constant for at least 20 consecutively generated sequences and only be changed thereafter. It is furthermore conceivable to increase the repetition of the same sequence and to keep constant the order in which the subgroups 1_1, 1_2, and 1_3 generate the stimuli 22 per cycle for at least 25 or at least 30 consecutively generated sequences. At this point, it is also noted that the sequences in the third partial figure of FIG. 9 are already varied after less than 20 sequences, for reasons of visualisation. This is, however, to be understood only as a simplified illustration of a sequence variation that is slow in comparison to the second partial figure of FIG. 9.

According to an embodiment, only the order in which the subgroups 1_1, 1_2, and 1_3 generate the stimuli 22 per sequence is varied in the CR stimulation shown in the third partial figure of FIG. 9. All other stimulation parameters can remain constant during the CR stimulation.

The variation of the sequences can, for example, take place stochastically or deterministically or in a mixed stochastic-deterministic manner.

Exactly as in the first and second partial figures, cycles in which stimulation breaks are observed can also be provided in the CR stimulation in accordance with the third partial figure of FIG. 9. For example, stimuli 22 can be generated during n consecutive cycles, and no stimuli 22 that are designed to suppress the pathologically synchronous and oscillatory neuronal activity can be generated during the following m cycles, where n and m are non-negative whole numbers. It is, however, conceivable that different stimuli that are not designed to suppress pathologically synchronous and oscillatory neuronal activity be applied during the stimulation breaks—in particular, with the subgroups 1_1, 1_2, and 1_3. It can also be provided that the subgroups 1_1, 1_2, and 1_3 not generate any stimuli during the stimulation breaks. The pattern of n cycles with stimulation and m cycles without stimulation can be continued periodically.

If it is provided for varying the sequences after a predefined number i of sequences (i≥20), the cycles without any stimulation are, in accordance with an embodiment, not counted, i.e., a variation of the order in which the subgroups 1_1, 1_2, and 1_3 generate the stimuli 22 only takes place in this embodiment when a sequence of stimuli 22 was actually respectively applied in i cycles. The number i after which the sequence is respectively varied can, for example, be determined in accordance with stochastic or deterministic or mixed stochastic-deterministic rules.

The variation of the sequences can furthermore take place at a constant rhythm, i.e., a variation always takes place, for example, after i cycles.

The CR stimulation with a slowly varying sequence is particularly suitable if stimulation can take place with stimulus strengths above threshold. It is then typically superior to the CR stimulation with a fixed sequence and to the CR stimulation with a quickly-varying sequence. If the side-effect threshold, i.e., the stimulus amplitude required to neutralise side effects, is reduced and/or side effects arise during the stimulation, a two-stage CR stimulation can be used. The advantage of the two-stage CR stimulation is that the first stage is applied with a stimulus strength below threshold, while stimulation only takes place above threshold in the second stage. Despite the comparatively particularly weak stimulus strength, the therapeutic effects are good and lasting.

A two-stage CR stimulation shall be explained below by way of example, with reference to the fourth, i.e., lowest, partial figure of FIG. 9. In the two-phase CR stimulation, stimulation takes place in the first stage with a rapidly varying sequence at a particularly low stimulus strength and, in the second stage, with a slowly varying sequence at a particularly high stimulus strength. In order to realise the two stimulation stages, the multi-channel electrode 40, or, in general, the stimulation unit 11, can be operated in two different stimulation modes (or operating modes). During a first time interval, which is called time interval 1 in the fourth partial figure of FIG. 9, the control unit 10 operates the contacts 41 of group 1 in a first stimulation mode. In the first stimulation mode, the control unit 10 controls group 1 such that the subgroups 1_1, 1_2, and 1_3 of group 1 repetitively generate sequences of stimuli 22, and the order in which the subgroups 1_1, 1_2, and 1_3 generate the phase-resetting stimuli 22 within a sequence is constant for at most 5 consecutively generated sequences and is then varied, wherein the strength of the stimuli 22 in the first stimulation mode is, in particular, less than or equal to a predefined stimulus strength. Otherwise, the stimuli 22 can be designed just as in the first through third partial figures of FIG. 9. The pattern, according to which the order in which the stimulation elements generate the stimuli within a sequence is constant for at most 5 consecutively generated sequences and is then varied, can be repeated several times.

The first time interval is followed by a second time interval, which is called time interval 2 in the fourth partial figure of FIG. 9. The second time interval can, in particular, follow directly after the first time interval, i.e., without an intermediate break. During the second time interval, the control unit 10 operates the subgroups 1_1, 1_2, and 1_3 of group 1 in the second stimulation mode. In the second stimulation mode, the control unit 10 controls the subgroups 1_1, 1_2, and 1_3 such that the subgroups 1_1, 1_2, and 1_3 repetitively generate sequences of phase-resetting stimuli 22, and the order in which the subgroups 1_1, 1_2, and 1_3 generate the stimuli 22 within a sequence is constant for at least 25 consecutively generated sequences and is then varied. The strength of the stimuli 22 in the second stimulation mode is, in particular, at least 1.3 times the predefined stimulus strength. The pattern, according to which the order in which the stimulation elements generate the stimuli within a sequence is constant for at least 25 consecutively generated sequences and is then varied, can be repeated several times.

It can, for the patient, be advantageous to carry out the change from the first stimulation mode to the second stimulation mode not in an abrupt, but in a fractional manner. An abrupt change from a stimulation strength below threshold in the first stimulation mode to a stimulation strength above threshold in the second stimulation mode can be very uncomfortable, e.g., painful. In order to design this transition to be more comfortable, habit-forming effects can be made use of by toggling the two stimulation modes several times within the course of the transition from the first time interval to the second time interval. The degree of the side effects, e.g., pain, depends not only upon the stimulation strength, but also upon the duration of the stimulus application. By applying short epochs in the second stimulation mode, the appearance of side effects can be significantly reduced. Habit-forming effects can even occur, so that the side effects in the later, permanently applied, second stimulation mode turn out to be less than without the fractional transition. The duration of the toggling between the first and second stimulation modes can vary, e.g., increase, over time within the course of the transition.

It is provided in the first phase, as described above, that the sequences remain constant for at most 5 consecutively generated sequences and be changed thereafter. The variation of the sequences can furthermore take place at a constant rhythm, i.e., a variation always takes place after $i_{Mode\_1}$ cycles, where $i_{Mode\_1}$ is a whole number from 1 to 5. The number of cycles after which the sequence is varied can alternatively be determined in accordance with stochastic or deterministic or mixed stochastic-deterministic rules. In the fourth partial figure of FIG. 9, a variation of the sequence takes place in each cycle of the first time interval, for reasons of visualisation.

According to an embodiment, in the two-phase CR stimulation, only the order in which the subgroups 1_1, 1_2, and 1_3 generate the stimuli 22 per sequence is varied. All other stimulation parameters can remain constant during the CR stimulation.

The variation of the sequences can, for example, take place stochastically or deterministically or in a mixed stochastic-deterministic manner.

It can be provided that the CR stimulation in the first stimulation mode take place continuously, i.e., sequences of stimuli 22 always be generated in consecutive cycles. Alternatively, breaks can, however, also be observed during the CR stimulation—in particular, during whole cycles. For example, stimuli 22 can be generated during $n_{Mode\_1}$ consecutive cycles, and no stimuli 22 that are designed to desynchronise the pathologically synchronous and oscillatory neuronal activity can be generated during the following $m_{Mode\_1}$ cycles, where $n_{Mode\_1}$ and $m_{Mode\_1}$ are non-negative whole numbers. The pattern of $n_{Mode\_1}$ cycles with stimulation and $m_{Mode\_1}$ cycles without stimulation can be continued periodically.

It is conceivable that different stimuli that are not designed to suppress pathologically synchronous and oscillatory neuronal activity be applied during the stimulation breaks—in particular, with the multi-channel electrode 40 or the stimulation unit 11. Alternatively, the multi-channel electrode 40 or the stimulation unit 11 does not generate any stimuli during the stimulation breaks.

If it is provided for varying the sequences after a predefined number $i_{Mode\_1}$ of sequences ($i_{Mode\_1} \leq 5$), the cycles without any stimulation are not counted according to one embodiment, i.e., a variation of the order in which the subgroups 1_1, 1_2, and 1_3 generate the stimuli 22 only takes place in this embodiment when a sequence of stimuli 22 was actually respectively applied in $i_{Mode\_1}$ cycles.

The strength of the stimuli 22, i.e., the amplitude of the stimuli 22, in the first stimulation mode is less than or equal to a predefined stimulus strength. The predefined stimulus strength can, in particular, be below threshold in the sense that, only during the stimulation, the stimuli 22 have desynchronising effects that, however, do not last beyond the end of the stimulation, i.e., after the end of the stimulation with the stimuli 22, the stimulus strength of which does not exceed the predefined stimulus strength, the desynchronising effect disappears.

As a result of the stimulation in the first stimulation mode, the neuronal population in the subregion stimulated by the group 1 is brought into a state in which it is significantly more receptive to the subsequent stimulation in the second stimulation mode with slowly varying sequence and higher stimulus strength.

With the exception of the number of cycles after which the sequence is varied and the stimulus strength, the stimulation in the second stimulation mode can have the same designs as the stimulation in the first stimulation mode explained above. The differences of the stimulation in the second stimulation mode in comparison to the stimulation in the first stimulation mode are explained below.

The fourth partial figure of FIG. 9 shows, in the second time interval, a CR stimulation in which the subgroups 1_1, 1_2, and 1_3 repetitively generate slowly varying sequences of stimuli 22 in the second stimulation mode. The order in which the subgroups 1_1, 1_2, and 1_3 generate the stimuli 22 within a sequence is kept constant for at least 25 consecutively generated sequences and is only varied thereafter. It is, furthermore, conceivable to increase the repetition of the same sequence and to keep constant in the second stimulation mode the order in which the subgroups 1_1, 1_2, and 1_3 generate the stimuli 22 per cycle for at least 30 or at least 35 consecutively generated sequences, for example.

The variation of the sequences in the second stimulation mode can take place at a constant rhythm, i.e., a variation always takes place, for example, after $i_{Mode\_2}$ cycles, where $i_{Mode\_2} \geq 25$. The number of cycles after which the sequence is varied can, alternatively, be determined in accordance with stochastic or deterministic or mixed stochastic-deterministic rules.

As in the stimulation in the first stimulation mode, in the stimulation in the second stimulation mode as well, only the order in which the subgroups 1_1, 1_2, and 1_3 generate the stimuli 22 per sequence can be varied. All other stimulation parameters can remain constant during the stimulation.

The variation of the sequences can, for example, take place stochastically or deterministically or in a mixed stochastic-deterministic manner.

In a second stimulation mode, the CR stimulation may take place continuously, i.e., sequences of stimuli 22 are always generated in successive cycles. Alternatively, breaks can, however, also be observed during the CR stimulation—in particular, during whole cycles. During $n_{Mode\_2}$ successive cycles, stimuli 22 may thus be generated, and, during the following $m_{Mode\_2}$ cycles, no stimuli 22 are generated that are designed to desynchronise pathologically synchronous and oscillatory neuronal activity, wherein $n_{Mode\_2}$ and $m_{Mode\_2}$ are non-negative whole numbers. The pattern of $n_{Mode\_2}$ cycles with stimulation and $m_{Mode\_2}$ cycles without stimulation may be continued periodically. The values for $n_{Mode\_2}$ and $m_{Mode\_2}$ of the second stimulation mode may, but need not, be identical to the values for $n_{Mode\_1}$ or, respectively, $m_{Mode\_1}$ of the first stimulation mode.

It is conceivable that other stimuli that are not designed to suppress synchronous and oscillatory neuronal activity be applied during the stimulation pauses—in particular, with the subgroups 1_1, 1_2 and 1_3. Alternatively, the subgroups 1_1, 1_2 and 1_3 generate no stimuli whatsoever during the stimulation pauses.

Insofar as it is provided for varying the sequences according to a predetermined number $i_{Mode\_2}$ of sequences ($i_{Mode\_2} \geq 25$), according to one embodiment, the cycles without stimulation are not counted as well, i.e., in this embodiment, a variation of the order in which the subgroups 1_1, 1_2 and 1_3 generate the stimuli 22 only occurs if a respective sequence of stimuli 22 was actually applied in $i_{Mode\_2}$.

The strength of the stimuli 22, i.e., the amplitude of the stimuli 22, amounts to at least 1.3 times the predetermined stimulus strength in the second stimulation mode. The strength of the stimuli 22 may, in particular, be so great that a pronounced and permanent therapeutic and/or desynchronising effect would be achieved if the stimuli 22 were applied during the entire stimulation duration, i.e., during the first and second time intervals. According to one embodiment, the lower bound for the stimulus strength in the second stimulation mode is greater than the 1.3 times of the predetermined stimulus strength, and amounts to 1.5 or 1.7 times the predetermined stimulus strength. Insofar as the stimuli 22 are electrical, current-controlled stimuli 22, the stimulus strength is provided by the amperage of the stimuli 22. In the event of optical stimuli 22, the stimulus strength may be the luminosity of the stimuli 22.

In the two-stage CR stimulation described here, the stimulus strength is dosed without loss or limitation of effectiveness. During the first stage, i.e., in the first stimulation mode, a subliminal stimulus strength is sufficient, whereby unwanted effects may be markedly reduced. Via the stimulation in the first stimulation mode, the stimulated neuron population is brought into a state in which it is markedly more sensitive to the stimulation that is subsequently performed in the second stage in the second stimulation mode. The two-stage CR stimulation consequently enables an improved stimulation effect, with simultaneously reduced side effects and other unwanted effects.

The underlying effective principle of the two-stage CR stimulation, viz., the enhancement of the desynchronising effect of the stimulation with slowly varying sequence via preceding stimulation with rapidly varying sequence, does not apply only for a subliminal stimulus strength of the stimulation with rapidly varying sequence. Rather, for a first stage above threshold, the effect of the two-stage CR stimulation at least tends to be better than all other variants of the CR stimulation of the same intensity and duration. In the event that the first stage with above-threshold stimulus strength is dispensed with, however, the particular advantage that side effects and other unwanted effects may be avoided or at least reduced via the use of the subliminal stimulation is lost.

Insofar as the device 2 depicted in FIG. 7 is used for the two-stage CR stimulation, i.e., a "closed loop" stimulation is performed, the control unit 10 may review the stimulation success using the measurement signals 23 received by the measurement unit 13 in reaction to the application of the stimuli 22.

As soon as a pronounced desynchronisation or acute clinical improvement or a pronounced improvement in the mental state of the patient has been established using the measurement signals 23, the first stimulation mode may be switched over to the second stimulation mode—in particular, with the aid of the control unit 10. In particular, an input unit coupled to the control unit 10 may be provided that may be operated by the patient and/or the treating physician and with which a switch may be made from the first stimulation mode into the second stimulation mode.

The stimulation success may, in particular, be checked by means of a threshold comparison. Depending upon which signals are used to determine the stimulation success, different threshold comparisons result. For example, if the pathological neuronal synchronisation is measured via the sensors of the measurement unit 13, e.g., EEG electrodes or deep electrodes (as an LFP signal), the decrease in the synchronisation by a predetermined value, e.g., by at least 20%, in comparison to the situation without stimulation is, according to experience, adequate for establishing a sufficient stimulation success and for changing from the first stimulation mode to the second stimulation mode. However, larger values, e.g., 50% or more, may be chosen in order to stimulate longer in the first stimulation mode, and thus with lower stimulus strength.

The clinical improvement is determined using typical changes in clinical scores or questionnaires that are known to the person skilled in the art. For example, related to these are the values Delta S, for a "minimal clinically relevant change", or even greater values, e.g., 2×Delta S, that are known from the literature.

In addition to the rule described above that determines the switching from the first stimulation mode to the second stimulation mode, an additional rule may be provided that acts on a slower time scale. If a therapeutic success has ceased over a predefined time period, e.g., 1 hour, the stimulation is deactivated. The therapeutic success is here measured as above, wherein the thresholds for a sufficient therapeutic success, e.g., a decrease in the initial synchronisation of 80%, may be preset by the user. If these thresholds are exceeded again for a predefined duration, e.g., 60 s, and/or the patient reports a mental state that is no longer sufficiently improved, the two-stage CR stimulation is restarted as described above.

With the aid of the measurement unit 13 of the device 2, values may be estimated for the lengths of the first time interval and the second time interval for a respective patient that are required in order to achieve the desired stimulation success. This information may subsequently be used for an application with the device 1, which possesses no measurement unit. In principle, the lengths of the first and second time intervals may be in the minute or hour range.

Furthermore, according to one embodiment, the predetermined stimulus strength can be determined with the aid of the measurement unit 13, from which predetermined stimulus strength results the upper or lower bound for the stimulus strengths in the first and second stimulation modes. This information may also be subsequently used in an application with the device 1. To determine the predetermined stimulus strength, the stimulation unit 11 is used in a first stimulation mode, for example, and the strength of the stimuli 22 is increased, starting from zero, until an acute effect appears, i.e., a reduction in the synchronisation of the stimulated neuron population, which, however, disappears again after the end of the stimulation. The predetermined stimulus strength may be derived from the stimulus strength obtained in this way, in that the predetermined stimulus strength is, for example, chosen from a range whose lower bound represents the stimulus strength at which a reduction in the synchronisation of the stimulated neuron population appears, and whose upper bound is, for example, 1.1 times the preceding stimulus strength.

In the preceding, the four different CR stimulation variants illustrated in the partial depictions from FIG. 9 were explained only by way of example, using group 1 and its subgroups 1_1, 1_2, and 1_3. The CR stimulation types described herein may have been accordingly applied to other groups of stimulation elements and their subgroups, as well as, in particular, the groups 2 and 3 shown in FIG. 8 and their subgroups.

It has, surprisingly, been shown that, for spatially inhomogeneous neuronal synchronisation processes, the stimulation results are especially good if stimulation is performed with the most suitable CR variant via the respective groups of stimulation elements. For this reason, in the case of multi-segment neurostimulation, the CR stimulation is individually applied as optimally as possible for each group of stimulation elements.

If side effects occur upon stimulation via a defined group of stimulation elements, and/or if the associated side effect threshold is reduced, stimulation occurs with lower amplitude and preferably two-stage CR stimulation. The intra-burst frequency, and thus the frequency within the pulse trains of a stimulus 22, may also be reduced, and, if applicable, the amplitude of the stimuli 22 may be increased in compensation.

If the device 2 depicted in FIG. 7 should be used in the sense of a "closed loop" variant, it may be advantageous to adapt the frequency $f_{stim}$ (=$1/T_{stim}$) of a respective group to the dominant frequency of the partial region of the target area that is stimulated by the corresponding group. The dominant frequency may be continuously or regularly measured in the respective partial region, e.g., via continuous or intermittent measurements, and the frequency $f_{stim}$ may be adapted accordingly.

In this way, different CR variants with respectively identical or different frequencies $f_{stim}$ may be applied via different groups of stimulation elements.

Such a stimulation is shown in FIG. 10 by way of example. Here, the groups 1, 2, and 3 of the multi-channel electrode 40 depicted in FIG. 8 apply different CR variants. Among other things, the stimuli 22 generated by the respective subgroups of the groups 1, 2, and 3 are plotted against time t in FIG. 10.

In the clinical testing of the individual groups by means of continuous high-frequency stimulation, and/or the testing by means of CR application, it resulted that side effects occurred and/or the side effect threshold was reduced in the patient, with stimulation via the groups 2 and 3. Therefore, a respective two-stage CR stimulation is applied via the groups 2 and 3, as was explained above in connection with the fourth partial illustration of FIG. 9. In the two-stage CR stimulation, a CR stimulation with rapidly varying sequence is applied in the first stage, i.e., in the first stimulation mode; by contrast, a CR stimulation with slowly varying sequence is applied in the second stage, i.e., in the second stimulation mode. For illustration purposes, respectively, only the first stage—the CR stimulation with rapidly varying sequence—is depicted in FIG. 10 for groups 2 and 3. In the present example, in this stage, the sequence is randomised from one cycle to the next.

Stimulation via group 1 led to no side effects and/or no decreased side effect threshold in the patient. Therefore, a CR stimulation with slowly varying sequence is administered via group 1, as it was explained above in connection with the third partial illustration of FIG. 9.

The dominant frequency of the pathological neuronal activity was also measured for each partial region stimulated by groups 1, 2, and 3. The period lengths $T_{stim}$ of groups 1, 2, and 3 were adapted to the respective measured dominant mean frequency. The corresponding period lengths of groups 1, 2, and 3 are designated in FIG. 10 as $T_{stim\_1}$, $T_{stim\_2}$, or $T_{stim\_3}$. For example, in general, the period length $T_{stim\_1}$ of a group i may be equated to the inverse of the dominant mean frequency of the pathological neuronal activity that was measured in the partial region stimulated by group i. According to one embodiment, the period length $T_{stim\_1}$ may be chosen in a range of 10 ms or 20 ms or 50 ms or 100 ms or 200 ms or 2,000 ms around the inverse of the dominant mean frequency of the pathological neuronal activity measured in the partial region stimulated by group i.

In the exemplary embodiment shown in FIG. 10, the CR stimulation applied via groups 1 and 2 has the same stimulation period, i.e., $T_{stim\_1}=T_{stim\_2}$, since the neuronal synchronisation processes to be stimulated via groups 1 and 2 have the same or a similar chronologically-averaged dominant frequency. The synchronisation process to be stimulated via group 3 has a smaller dominant mean frequency and is accordingly stimulated with the longer stimulation period $T_{stim\_3}$. In this way, the neuronal synchronisation processes associated with the different groups 1, 2, and 3 are specifically stimulated—according to anatomical distribution (via selection of the electrodes and selection of the stimulus amplitude of the respective contact), dynamic characteristics (in particular, with regard to the dominant frequency which determines the respective period length $T_{stim}$), and side effect profile.

In general, with the stimulation type described in the preceding, at least one first group of stimulation elements and one second group of stimulation elements generate sequences of stimuli repetitively in a respective time pattern that consists of successive cycles. The sequences of stimuli that are generated by the first group differ from the sequences of stimuli generated by the second group.

The difference between the sequences generated by the two groups may lie in the number of successively generated sequences, after which the order of the stimulation elements is varied within a sequence. For example, the first group may implement a two-stage CR stimulation, as it is depicted by way of example in the fourth partial illustration of FIG. 9. In this instance, in the first stimulation mode, the order in which the stimulation elements generate the stimuli within a sequence is constant for the first group for at most 5 successively generated sequences, and after this is varied, and, in the second stimulation mode, the order in which the stimulation elements within a sequence generate the stimuli is constant for at least 25 successively generated sequences and is subsequently varied. For example, the second group may also implement a CR stimulation with a slow variation of the sequences, as it is shown by way of example in the third partial illustration of FIG. 9. The order in which the stimulation elements of the second group generate stimuli within a sequence is then held constant for at least 20 successively generated sequences and is subsequently varied.

Additional groups of stimulation elements may also be provided that, for example, generate sequences of stimuli identical to those of the first or second group, or also different sequences of stimuli. For example, a third group of stimulation elements may implement a CR stimulation, as it is shown by way of example in the second partial illustration of FIG. 9, and, in particular, a fourth group of stimulation elements may implement a CR stimulation, as it is shown by way of example in the first partial illustration of FIG. 9.

Additionally or alternatively, the sequences of stimuli that are generated by the first, second, and possibly additional groups differ in the duration of the respective cycles. This is shown by way of example in FIG. 10. Here, group 1 has a cycle duration $T_{stim\_1}$, and group 3 has a cycle duration $T_{stim\_3}$, wherein $T_{stim\_1} < T_{stim\_3}$.

Instead of the CR stimulation, however, other desynchronising stimulation methods may also be used.

Surprisingly, it has been shown that the combined application of CR stimulation with continuous high-frequency stimulation in respective different segments may be advantageous. Applied individually, the continuous high-frequency stimulation, in which pulses are periodically administered with a repetition frequency of at least 100 Hz, typically has no long-lasting desynchronising effects. If, for example, with a spatially inhomogeneous neuronal synchronisation process, the measurements results in the dominant frequencies of the different partial regions varying strongly, and/or the bounds of the respective partial regions even varying chronologically for good measure, it is advantageous to effectively deactivate some partial regions temporarily via charging with continuous high-frequency stimulation, and, in the meanwhile, to treat the partial regions that are not deactivated with CR stimulation. For this, a continuous high-frequency stimulation is then applied via all or some or only one contact of a group, while the other groups are stimulated with respective, individually-adapted CR stimulation. This stimulation principle may be applied quasi-iteratively, i.e., step-by-step, to the neuronal synchronisation process remaining after successful CR stimulation. For each step of this iterative method, suitable groups or segments are selected for stimulation, until no, or no clinically disruptive, neuronal synchronisation remains at the conclusion.

In this iterative procedure, the success of the CR stimulation may be clinically detected and/or be checked within the scope of a "closed loop" variant and/or be checked by occasional, and thus discontinuously used, sensors. The objective estimation of the stimulation success is determined by the decrease in the amplitude of the pathological neuronal synchronisation.

The combined application of CR stimulation and continuous high-frequency stimulation may also be advantageous if, for example from a medical indication, no signals may be derived via additional implanted electrodes, and the treatment effect does not appear sufficiently quickly.

The goal of the iterative, multi-channel stimulation is to treat with CR stimulation smaller regions that can be better controlled via stimulation. For example, the chronological variability of the dominant frequency of the region to be treated may be reduced, in that the partial region that is to be stimulated belongs to only one segment of an extremity, and thus is driven only with a predominantly mechanically-dependent eigenfrequency via the proprioceptive feedback (thus, via neuronal signals of the proprioception of the extremity).

Figure 11:
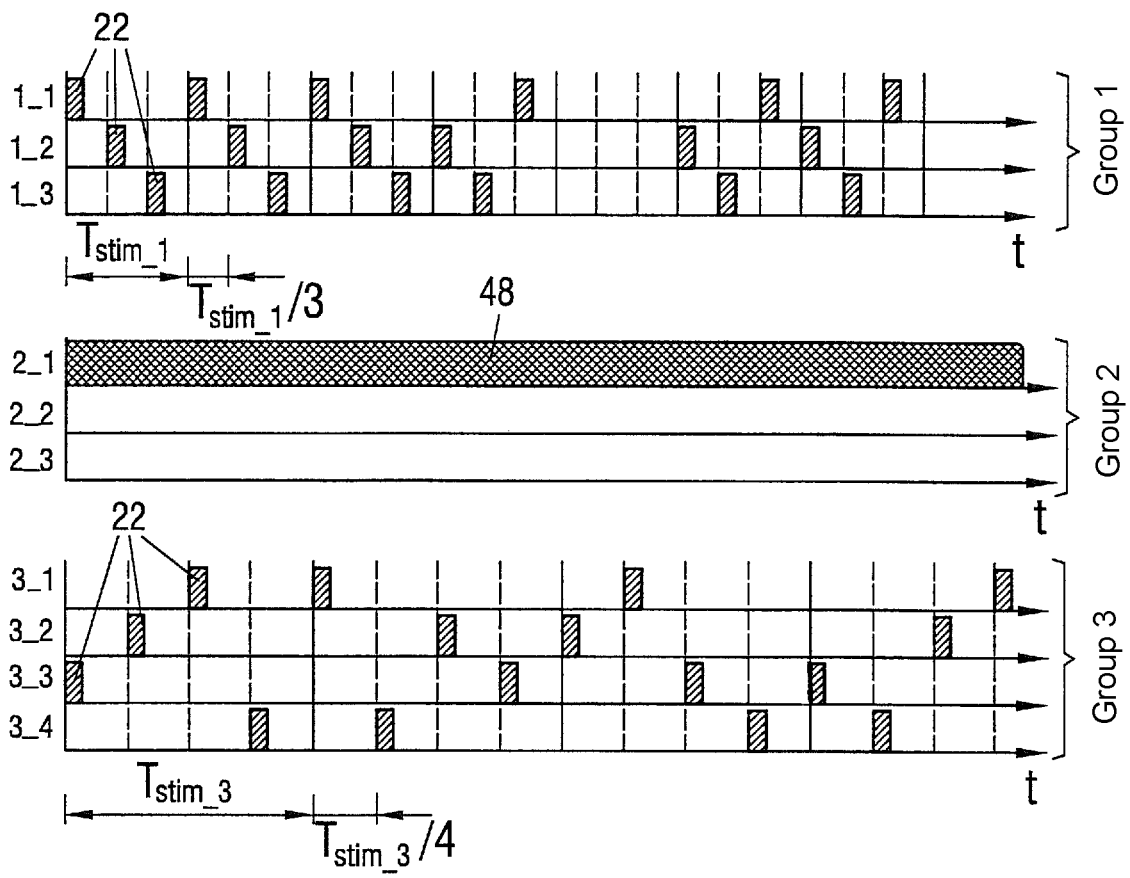
FIG. 11 illustrates a schematic illustration of an iterative multi-channel stimulation.

FIG. 11 shows a stimulation applied with the multi-channel electrode 40 depicted in FIG. 8, in which a CR stimulation adapted to the respective stimulated partial region of the target area is applied via groups 1 and 3. The CR stimulations applied by groups 1 and 3 correspond to the CR stimulations from FIG. 10.

In comparison to FIG. 10, in FIG. 11, stimulation via group 2 occurs, not with CR stimulation, but rather with standard, continuous high-frequency stimulation. A periodic pulse train having a pulse rate, i.e., a repetition frequency of the pulses, of more than 100 Hz is hereby applied continuously, i.e., without pause. The pulses of the pulse train may, in particular, be identical. In FIG. 11, the standard continuous high-frequency stimulation is characterised by a continuous horizontal bar 48. The standard, continuous high-frequency stimulation may be applied via a single subgroup or multiple subgroups or all subgroups of the respective group. In FIG. 11, by way of example, the standard, continuous high-frequency stimulation is applied only via the subgroup 2_1. A "continuous" application of the periodic pulse train here means that the periodic pulse train is applied by a different group—at least during the application of the parallel CR stimulation.

The stimulation type depicted in FIG. 11 is applied, since it may prove to be advantageous to stimulate spatially-extended neuronal synchronisation processes with qualitatively different stimulation methods. The associated synchronous regions may be inhibited and/or blocked via the standard, continuous high-frequency stimulation, whereby the therapeutic alteration of the synaptic connectivity in the two different neural regions takes place markedly more quickly.

For this, a continuous high-frequency stimulation is then applied via all or some or only one contact(s) of a group, while the other groups apply a CR stimulation. The CR stimulation may thereby be respectively individually adapted; in particular, a selection may be made from the four different CR stimulus sequences described in connection with FIG. 9. This stimulation principle may be applied quasi-iteratively, i.e., step-by-step, to the neuronal synchronisation process remaining after successful CR stimulation. For each step of this iterative method, suitable groups or segments are selected for stimulation, until no, or no clinically disruptive, neuronal synchronisation remains at the conclusion.

Figure 12:
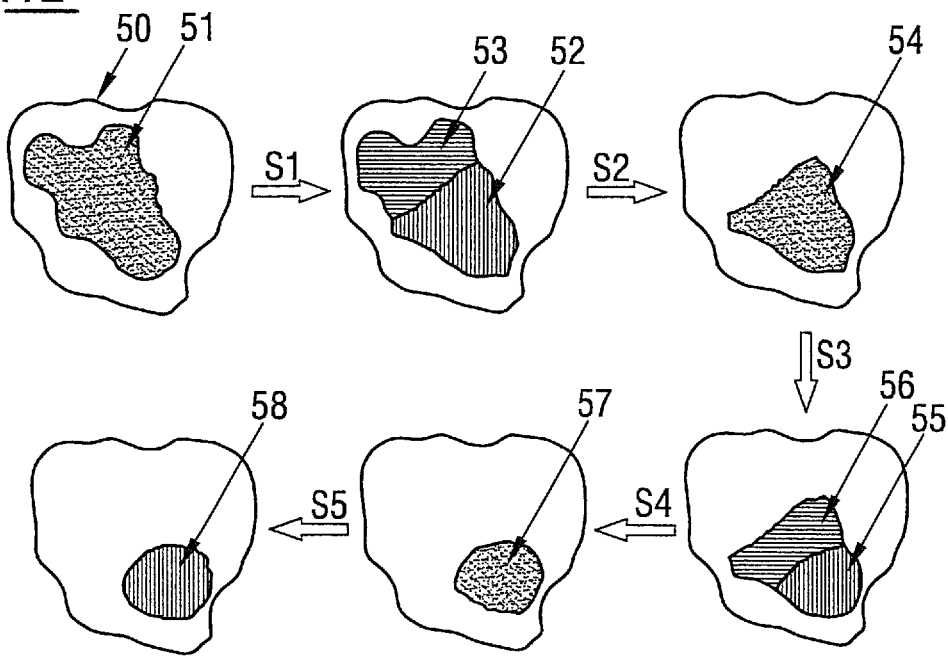
FIG. 12 illustrates a schematic illustration of the principle of the iterative multi-channel stimulation.

FIG. 12 illustrates the principle of the iterative multi-channel stimulation by way of example. The schematic depiction shows a target area 50 in the brain and/or spinal cord of a patient in which a neuronal synchronisation process that is inhomogeneous with regard to its functional characteristics is located in a spatially-circumscribed region 51. In step S1, with the aid of a first group of stimulation elements, a partial region 52 is charged with a standard, continuous high-frequency stimulation, whereas, with the aid of a second group of stimulation elements, a partial region 53 is stimulated with CR stimulation. Ultimately, the pathological neuronal synchronisation in the partial region 53 disappears via the CR stimulation, such that a pathological neuronal synchronisation still remains only in a partial region 54 (see step S2). In step S3, with the aid of a third group of stimulation elements, a partial region 56 is stimulated with CR stimulation, and, with the aid of a fourth group of stimulation elements, a partial region 55 is stimulated with standard, continuous high-frequency stimulation, wherein the third and fourth groups respectively contain at least some of the stimulation elements of the first group. Ultimately, pathological neuronal synchronisation still remains only in a partial region 57 (see step S4). Ultimately, with the aid of a fifth group of stimulation elements, a partial region 58 is stimulated in step S5 exclusively by means of CR stimulation, such that, at the end, no or barely any pathological neuronal synchronisation remains.

The simultaneous stimulation of a partial region of the target area with standard, continuous high-frequency stimulation and of one or more other partial regions with CR stimulation may, for example, take place until it is established, using the measurement signals 23 received by the measurement unit 13, that the degree of synchronisation of the neurons stimulated with the CR stimulation sequences has been reduced by at least one predetermined threshold in comparison to the state before the CR stimulation. The duration obtained from this may be used for an application with the device 1, which possesses no measurement unit. In this instance, the simultaneous stimulation of a partial region of the target area with standard, continuous high-frequency stimulation and of one or more other partial regions with CR stimulation may be ended after a predetermined duration, for example. In principle, the duration of such a stimulation may be in the minute or hour range.

Figure 13:
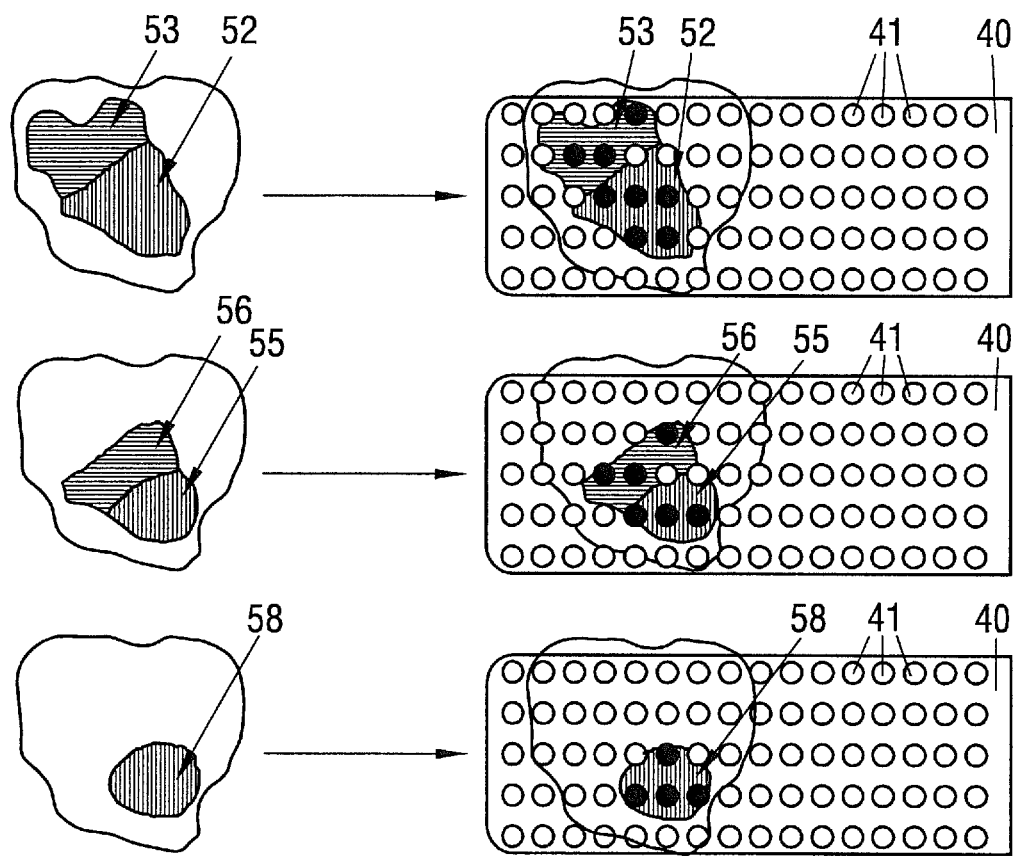
FIG. 13 illustrates schematic illustrations of the contacts of a multi-channel electrode used for the iterative multi-channel stimulation.

FIG. 13 is a schematic illustration of the contacts 41 of a multi-channel electrode 40 for stimulation of the partial regions 52 and 53 (see upper partial illustration), of the partial regions 55 and 56 (see middle partial illustration), and of the partial region 58 (see lower partial illustration), said contacts being used for the iterative, multi-channel stimulation from FIG. 10, for example. The contacts 41 used for stimulation are respectively coloured dark and clarify the first through fifth groups of stimulation elements.

The individual components of the devices 1 and 2—in particular, the control unit 10, the stimulation unit 11, and/or the measurement unit 13—may be structurally separate from one another. Therefore, the devices 1 and 2 may also be construed as systems. To implement its tasks, the control unit 10 may contain a processor—for example, a microcontroller. The stimulation methods described here may be stored as software code in a memory associated with the control unit 10.

Figure 14:
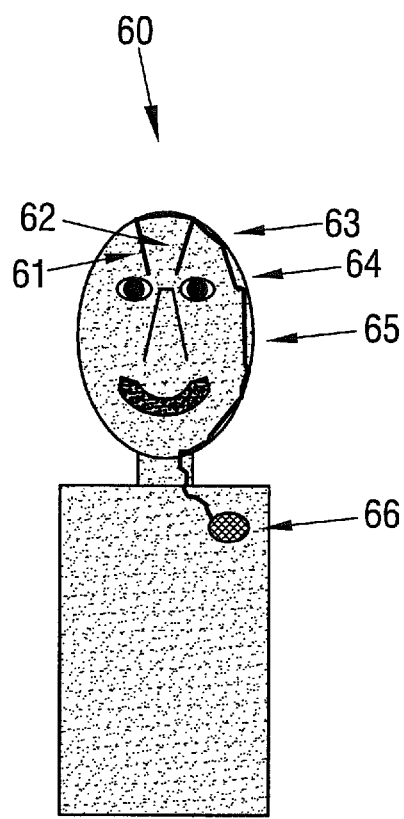
FIGS. 14 & 15 illustrates schematic illustrations of devices for the invasive electrical stimulation of neurons.

FIG. 14 schematically shows a device 60 for invasive electrical stimulation of neurons with a pathologically synchronous and oscillatory neuronal activity, according to one embodiment of the invention. The device 40 comprises two multi-channel electrodes 61, 62 that are implanted in the brain of the patient and connected via cable 63 to a connector 64. The connector 64 in turn is connected via a cable 65 to a control unit 66. The device 60 may have the functions of the devices 1 and 2 described above.

Figure 15:
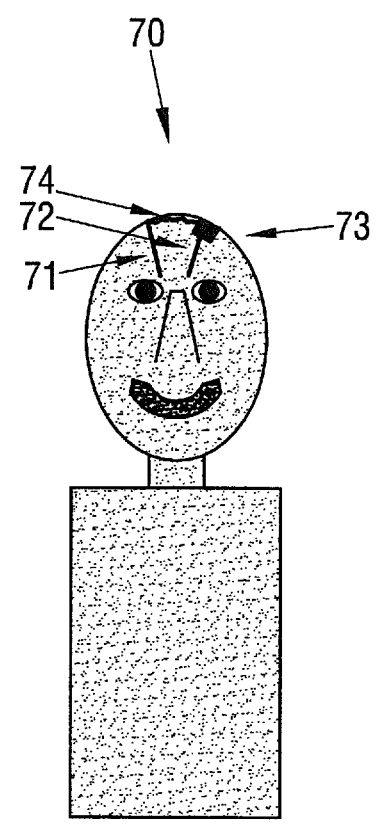

FIG. 15 schematically shows an additional device 70 for invasive electrical stimulation of neurons with a pathologically synchronous and oscillatory neuronal activity, according to one embodiment of the invention. In the same manner as the device 60, the device 70 comprises two, implanted, multi-channel electrodes 71, 72. The device 70 also comprises a generator 73 implanted in the bore hole, which generator is directly connected to the multi-channel electrode 72. The multi-channel electrode 71 is connected to the generator 73 via a cable 74.

The device according to the invention may possess multi-channel electrodes, as, for example, they are depicted in FIGS. 4 and 8, and/or other multi-channel electrodes. For multi-channel electrodes, stimulation or measurement contacts of differing geometry may be used. Contacts of differing geometry may also be structurally joined. In FIGS. 16 and 17, a multi-channel electrode 80 with annular contacts 81 is depicted by way of example. For example, stimulation takes place here via dark-marked contacts 81, whereas stimulation does not take place via white-marked contacts 81.

In FIG. 16, the group 1 comprises the subgroups 1_1, 1_2, and 1_3, and the group 2 comprises the subgroups 2_1, 2_2, 2_3, and 2_4, wherein, in this example, each subgroup consists of precisely one contact 81. In FIG. 17, the subgroup 2_1 is comprised of two contacts 81. The stimulations described in this application may be applied via the groups 1 and 2.

Implantable stimulation units for the optical stimulation of neuronal tissue are known. For example, a light source, such as a laser, a laser diode, or an LED, may generate a light beam that is distributed with the aid of a light injection to the inputs of a fibre bundle consisting of multiple optical waveguides. A control unit thereby specifies, for example, at which point in time an individual light pulse or a train of light pulses is injected into which fibres of the fibre bundle. The output points of the individual fibres of the fibre bundle, i.e., the ends of the fibre, are situated at various locations in the target area in the brain and/or spinal cord of the patient. The light thus stimulates different sites of the target area in a chronological sequence provided by the control unit. However, other implantable stimulation units may also be used that are suitable for direct optical stimulation of neuronal tissue.

As described above, in the CR stimulation, the stimuli 22 produce a reset of the phase of the neuronal activity of the stimulated neurons. The phase reset of the individual stimuli 22 may be checked with the aid of the measurement signals 23 received by the measurement unit 13. Such an examination may be performed before the actual therapeutic neurostimulation.

For this, a signal which sufficiently represents the activity of the sub-population stimulated via the j-th stimulation channel is measured via a sensor of the measurement unit 13. This signal is received either directly from the sub-population via a non-invasive measurement, e.g., via EEG or MEG electrodes, or an invasive measurement, e.g., via implanted electrodes, as a surface EEG, or as a local field potential and/or derivatives of groups of individual neurons (multi unit activity=MUA) via deep electrodes. The signal may also be determined indirectly via the measurement of a variable correlated with the activity of the stimulated sub-population. Suitable for this are, for example, EEG/MEG/LFP/MUA signals of the neuronal activity of a different neuron population closely coupled with this sub-population, or associated electromyography, accelerometer, or gyroscope signals.

Since neuronal signals typically contain rhythmic activity in different frequency bands, in such instances, it is advantageous to determine—for example, by means of bandpass filtering or wavelet analysis or empirical mode decomposition—the signal $x_j(t)$, which represents the pathological oscillatory activity of the sub-population stimulated by the j-th stimulation channel.

An only slightly complicated procedure for checking the phase reset is to determine the mean stimulus response. For this, a stimulus with identical stimulus parameters is applied at the times $T_1, T_2, \ldots, T_I$. The spacings between the individual stimuli $T_{k+1}-T_k$ should be sufficiently large and randomised, i.e., not constant, in order to avoid transient phenomena (see P. A. Tass: Transmission of stimulus-locked responses in two coupled phase oscillators. Phys. Rev. E 69, 051909-1-24 (2004)). The spacings $T_{k+1}-T_k$ should typically be in the range of at least ten times—better, one hundred times—the mean period of the pathological oscillation. The stimulus response averaged over all I test stimuli is calculated according to the following equation:

$$\bar{x}_j(t) = \frac{1}{I} \sum_{k=1}^{I} x_j(\tau_k + t) \quad (1)$$

If the spacings $T_{k+1}-T_k$ between the individual stimuli are sufficiently large, an averaged stimulus response is received in the pre-stimulus range, i.e., in the range before the application of a respective stimulus (see P. A. Tass: Transmission of stimulus-locked responses in two coupled phase oscillators. Phys. Rev. E 69, 051909-1-24 (2004)). A phase reset may be established if a mean stimulus response can be detected, i.e., if a stimulus response different than zero is found in the post-stimulus range, i.e., in a range for t>0, wherein t=0 represents the starting point in time of the respective stimulus. This may be determined via visual inspection. It may also be possible to have this performed by device 2—in particular, the control unit 10—in that the pre-stimulus distribution of $\bar{x}_j(t)$ or $|\bar{x}_j(t)|$ is considered and a characteristic threshold is determined, e.g., the 99th percentile of the pre-stimulus distribution of $|\bar{x}_j(t)|$, or simply its maximum. For example, if the absolute value of the post-stimulus response now exceeds this characteristic threshold, in principle or for a predetermined minimum duration, e.g., 20 ms, a mean response differing from zero is present. In this instance, a phase reset may be present. This means that the stimulus strength would need to be increased until the post-stimulus response differs from a zero line. In addition to the simple method proposed here—which has, however, been proven in practice—other statistical tests known to the person skilled in the art may also be used for signal analysis.

The analysis of the phase offers a more precise, but more complicated variant for testing whether the stimuli produce a phase reset. For this, the phase $\psi_j(t)$ of $x_j(t)$ is determined. This takes place by means of Hilbert transformation from the signal determined by means of bandpass filtering or empirical mode decomposition, which signal represents the pathological oscillatory activity. In comparison to bandpass filtering, empirical mode decomposition enables a parameter-independent determination of physiologically relevant modes in different frequency ranges (cf. N. E. Huang et al.: The empirical mode decomposition and the Hilbert spectrum for nonlinear and non-stationary time series analysis. Proc. R. Soc. A: Math. Phys. Eng. Sci. 454:903-995 (1998)). The combination of empirical mode decomposition with subsequent Hilbert transformation is referred to as Hilbert-Huang transformation (cf. N. E. Huang et al.: A confidence limit for the empirical mode decomposition and Hilbert spectral analysis, Proceedings of the Royal Society of London Series A, 459, 2317-2345 (2003)). The phase $\psi_j(t)$ may also be determined by means of wavelet analysis.

A phase reset is present if the phase $\psi_j(t)$ is set to a preferred value via a stimulus (with stimulus beginning at t=0) after a specific time. This means that $\{\psi_j(\tau_k+t)\}_{k=1,\ldots,I}$, the distribution of values of the phase $\psi_j(t)$ obtained by the I stimulus responses, has an accumulation value at time t (relative to the burst beginning at t=0). Different methods with which it can be demonstrated that a distribution has an accumulation value (thus, a peak) are known to the person skilled in the art. One customary method is the determination of the phase reset index $\rho(t)$ by means of circular mean value:

$$\rho(t) = \left| \frac{1}{I} \sum_{k=1}^{I} \exp[i\psi_j(\tau_k + t)] \right| \quad (2)$$

A phase reset is present if $\rho(t)$ exceeds, for example, the maximum or the 99th percentile of the pre-stimulus distribution of $\rho(t)$ (at one point in time or within a small time window of, for example, 20 ms).

In practice, the analysis with the mean responses $\bar{x}_j(t)$ has proven to be sufficient.

For a stimulus 22 designed as a pulse train, which stimulus should produce a phase reset, the duration of the individual pulses, the amplitude of the individual pulses, the frequency with which the pulses are periodically repeated in the pulse train, and the number of pulses in the pulse train must be determined. For the respective patient and stimulation site, the stimulus parameters that lead to a phase reset of the neuronal activity can be found, in that, typically, three of the parameters cited in the preceding are chosen as constants, and one parameter is varied.

The invention claimed is:

1. A device for stimulating neurons, comprising:
   a stimulation unit configured to be implanted into a body of a patient and including a plurality of stimulation elements for stimulating neurons in a target area of a brain and/or spinal cord of the patient with stimuli; and
   a control unit which actuates the stimulation unit such that multiple groups of stimulation elements respectively generate the stimuli,
   wherein the multiple groups respectively comprise a plurality of stimulation elements of the stimulation unit,
   wherein a first group and a second group of the multiple groups respectively generate sequences of stimuli in a repetitive manner in a respective time pattern which consists of successive cycles, and
   wherein the sequences of stimuli generated by the first group differ from the sequences of stimuli generated by the second group in the number of successively generated sequences subsequent to which the order in which the stimulation elements within a sequence generate the stimuli is varied, and/or in a duration of the respective cycles,
   wherein the control unit actuates the stimulation elements of the second group such that the order in which the stimulation elements generate the stimuli within a sequence is constant for at least 20 sequences generated in succession, and then is varied.

2. The device according to claim 1, wherein the time pattern, according to which the order in which the stimulation elements generate the stimuli within a sequence is constant for at least 20 sequences generated in succession and then the order is varied, is repeated multiple times.

3. The device according to claim 1, wherein the stimuli are configured to desynchronise a pathologically synchronous and oscillatory activity of neurons, when administered to the patient.

4. The device according to claim 1, wherein the stimuli generated by the stimulation elements are configured such that a phase of a neuronal activity of the stimulated neurons is reset.

5. The device according to claim 1, wherein the first group and the second group respectively generate either precisely one sequence of stimuli or no stimuli within a respective cycle.

6. The device according to claim 1, wherein each of the stimulation elements of the first and second groups generates no more than precisely one stimulus within a respective sequence of stimuli.

7. The device according to claim 6, wherein precisely one stimulus is precisely one electrical pulse train and/or precisely one optical pulse or pulse train.

8. The device according to claim 1, wherein each of the groups has one or more subgroups, and the subgroups respectively comprise at least one of the stimulation elements belonging to the respective group, wherein the stimulation elements, in particular, of a respective subgroup simultaneously generate the same stimuli, and wherein the device, in particular, has a number of independent current sources that is greater than or equal to the number of subgroups used for stimulation.

9. The device according to claim 1, wherein the target area comprises multiple partial regions, and the multiple groups of stimulation elements respectively stimulate a partial region of the target area with the stimuli.

10. The device according to claim 9, comprising a measurement unit configured to receive measurement signals that reproduce a neuronal activity of the neurons stimulated with the stimuli, wherein the control unit, using the measurement signals, determines a dominant frequency of a synchronous and oscillatory neuronal activity for each of the partial regions of the target area that are stimulated by the first and second groups.

11. The device according to claim 9, wherein the control unit is configured to adapt a duration of the cycles for each of the first and second groups to an inverse of the dominant frequency of a synchronous and oscillatory neuronal activity that is determined for the respective partial region.

12. A method for stimulating neurons, comprising:
implanting a stimulation unit into the body of a patient, with a plurality of stimulation elements that stimulate neurons in a target area of a brain and/or spinal cord of the patient with stimuli;
generating, by multiple groups of stimulation elements, respectively, the stimuli, wherein the multiple groups comprise a plurality of stimulation elements of the stimulation unit;
generating by a first group and a second group of the multiple groups, respectively, sequences of stimuli in a repetitive manner in a respective time pattern which consists of successive cycles;
generating the sequences of stimuli by the first group that differ from the sequences of stimuli generated by the second group in the number of successively generated sequences subsequent to which the order in which the stimulation elements within a sequence generate the stimuli is varied, and/or in a duration of the respective cycles; and
actuating the stimulation elements of the second group such that the order in which the stimulation elements generate the stimuli within a sequence is constant for at least 20 sequences generated in succession, and then is varied.

13. A non-transitory computer readable medium having software stored thereon for execution in a data processing system, wherein the software, when executed by a processor, is configured to:
generate control signals for actuating a stimulation unit implanted in the body of a patient, wherein the stimulation unit comprises a plurality of stimulation elements for stimulating neurons in a target area of a brain and/or spinal cord of the patient with stimuli, wherein the control signals actuate the stimulation unit such that multiple groups of stimulation elements respectively generate the stimuli,
wherein the multiple groups respectively comprise a plurality of stimulation elements of the stimulation unit,
wherein a first group and a second group of the multiple groups respectively generate sequences of stimuli in a repetitive manner in a respective time pattern which consists of successive cycles,
wherein the sequences of stimuli generated by the first group differ from the sequences of stimuli generated by the second group in the number of successively generated sequences subsequent to which the order in which the stimulation elements within a sequence generate the stimuli is varied, and/or in a duration of the respective cycles, and
wherein the stimulation elements of the second group are actuated such that the order in which the stimulation elements generate the stimuli within a sequence is constant for at least 20 sequences generated in succession, and then is varied.

* * * * *